US007448996B2

(12) United States Patent
Khanuja et al.

(10) Patent No.: US 7,448,996 B2
(45) Date of Patent: Nov. 11, 2008

(54) METHOD AND APPARATUS FOR REMOTELY MONITORING THE CONDITION OF A PATIENT

(75) Inventors: Sukhwant Singh Khanuja, Chicago, IL (US); Sandeep Garg, Naperville, IL (US); Irwin Preet Singh, Prospect Heights, IL (US)

(73) Assignee: Carematix, Inc., Chicago, IL (US)

( * ) Notice: Subject to any disclaimer, the term of this patent is extended or adjusted under 35 U.S.C. 154(b) by 0 days.

(21) Appl. No.: 10/414,326

(22) Filed: Apr. 15, 2003

(65) Prior Publication Data

US 2004/0102683 A1 May 27, 2004

Related U.S. Application Data

(60) Provisional application No. 60/372,894, filed on Apr. 16, 2002.

(51) Int. Cl.
*A61B 5/00* (2006.01)

(52) U.S. Cl. ....................... 600/300; 600/301; 128/903; 128/904; 128/905; 128/920; 705/2; 705/3; 705/4

(58) Field of Classification Search ................. 600/300, 600/301; 128/920, 903–905; 709/203; 705/2–4
See application file for complete search history.

(56) References Cited

U.S. PATENT DOCUMENTS 5,673,692 A * 10/1997 Schulze et al. .............. 600/301
6,294,999 B1 9/2001 Yarin et al.
6,401,085 B1 6/2002 Gershman et al.
6,440,068 B1 8/2002 Brown et al.
6,478,736 B1 * 11/2002 Mault .......................... 600/300
6,544,173 B2 4/2003 West et al.
6,599,250 B2 * 7/2003 Webb et al. ................. 600/300

* cited by examiner

*Primary Examiner*—Max Hindenburg
*Assistant Examiner*—Kai Rajan
(74) *Attorney, Agent, or Firm*—McAndrews, Held & Malloy, Ltd.

(57) ABSTRACT

A patient monitoring system provides enhanced functional capability relative to known systems and provides a wireless communication link between a patient monitoring device, worn by a patient, and a local hub. The patient monitoring system is adapted to monitor various patient physiological characteristics, such as blood pressure, pulse rate, blood glucose, weight, pulse oximetry and others. The data from the patient monitoring device is wirelessly transmitted to a local hub, which, in turn, is configured to automatically transfer the data to a remote server, for example, over a public or private communications network. In one embodiment of the invention, the server is configured as a web portal to selectively allow access to such patient physiological data by designated third parties, such as physicians, clinicians, relatives and the patient themselves.

27 Claims, 25 Drawing Sheets

| Select | Date | Time | Systolic | Diastolic | PPM | Annotation |
|---|---|---|---|---|---|---|
| ☐ | 10-24-2002 | 07:41:12 PM | 143.0 | 84.0 | 73.0 | |
| ☐ | 10-24-2002 | 08:55:09 PM | 146.0 | 87.0 | 72.0 | |
| ☐ | 10-25-2002 | 11:33:51 AM | 149.0 | 87.0 | 74.0 | |
| ☐ | 10-27-2002 | 09:32:51 AM | 152.0 | 89.0 | 75.0 | |
| ☐ | 10-28-2002 | 09:25:33 PM | 151.0 | 83.0 | 73.0 | |
| ☐ | 10-29-2002 | 10:02:03 PM | 145.0 | 80.0 | 73.0 | |
| ☐ | 10-30-2002 | 11:00:33 PM | 141.0 | 83.0 | 77.0 | |
| ☐ | 10-31-2002 | 10:12:53 PM | 138.0 | 81.0 | 74.0 | |
| ☐ | 11-01-2002 | 08:58:03 PM | 135.0 | 80.0 | 76.0 | |

244

252

254

METHOD AND APPARATUS FOR REMOTELY MONITORING THE CONDITION OF A PATIENT

CROSS REFERENCE TO RELATED APPLICATIONS

This application claims the benefit and priority of U.S. provisional patent application No. 60/372,894, filed on Apr. 16, 2002.

BACKGROUND OF THE INVENTION

1. Field of the Invention

The present invention relates to a patient monitoring system and more particularly to a patient monitoring system for monitoring various physiological characteristic data of a patient, such as blood pressure, pulse rate, blood glucose, weight and others, which wirelessly transmits such data to a hub, located near the patient, which, in turn transfers the data automatically to a remote server, for example, over a public or private communications network, which, in one embodiment, the remote server is configured as a web portal which selectively allows access to patient data by selected third party users, such as physicians, clinicians, patients, and/or relatives, and, in addition provides increased functionality relative to known systems by enabling trends of the patient data to be developed as well as automatically generate communications with the patient or other third parties by way of e-mail or pager when predetermined thresholds for selected physiological characteristics are exceeded and/or to remind the patient to take physiological measurements.

2. Description of the Prior Art

Healthcare costs have been increasing at a tremendous rate for the past decade, far exceeding the rate of inflation. The compound average growth rate for healthcare spending over the past decade was 6%, amounting to nearly $1.3 trillion in the year 2001. Chronic disease patients, whose numbers have doubled during the same decade, account for nearly $700 billion of this spending. Managed care organizations have begun to seek help from disease management companies to contain the spending on chronic diseases. Disease management companies thus have developed systems to monitor the chronically ill patients and help lower healthcare spending by improving patient compliance to medication schedules thereby lowering the hospitalization rates.

Various types of patient monitoring systems are known. For example, U.S. Pat. Nos. 5,810,747 and 5,694,940 disclose patient monitoring systems in which the patient monitoring devices are hard wired to a local hub, which, in turn, is connected to a remote station, for example, over a communication network. The fact that the patient monitors are hard wired to the local station significantly reduces the utility of such systems. For example, such systems are obviously not suitable for ambulatory patients and many applications where it may be desired to remotely monitor the physiological characteristics of a patient outside of a non-clinical environment.

Accordingly, various systems have been developed in which the patient monitoring device, normally worn by a patient, is connected by way of a wireless link to a local hub, which, in turn, is connected to a remote station or server by way of a public communication network, such as the plain old telephone system (POTS). Examples of such systems are disclosed in U.S. Pat. Nos. 3,882,277; 5,522,396; and 6,093,146. Each of these systems include a patient monitoring device, connected to a local hub by way of a wireless link, which, in turn, is connected to a remote server by way of a public communication link, such as POTS. Such systems depend on the use of telephone modems which require patients to place a phone receiver into a modem cradle and dial up the remote server. Such systems have been found to be far too complicated and difficult for elderly and critically ill patients.

In order to resolve this problem, patient monitoring systems, for example, as disclosed in U.S. Pat. No. 6,336,900, have been developed, which not only provide a wireless link between the patient monitor and the local hub, but also automatically dial and connect to the remote server to facilitate the transfer of the physiological data to the remote server. Unfortunately, the functional capability of such systems is relatively limited. For example, such systems only provide limited access to the patient data. In addition, such systems can not be used to provide reminders to patients to take readings or provide messages to the patients or third parties when the physiological characteristics of a patient exceed predetermined thresholds. Thus, there is a need for a patient monitoring system for monitoring the physiological characteristics of a patient that provides enhanced functionality and expanded access to the healthcare data while not tethering the patient to a local hub, thereby improving patient compliance, affording the healthcare provider the ability to capture adverse events sooner and avoid costly emergency care and reduce costly home health visits.

SUMMARY OF THE INVENTION

Briefly, the present invention relates to a patient monitoring system which provides enhanced functional capability relative to known systems and provides a wireless communication link between a patient monitoring device, worn by a patient, and a local hub. The patient monitoring system in accordance with the present invention is adapted to monitor various patient physiological characteristics, such as blood pressure, pulse rate, blood glucose, weight, pulse oximetry and others. The data from the patient monitoring device is wirelessly transmitted to a local hub, which, in turn, is configured to automatically transfer the data to a remote server, for example, over a public or private communications network. In one embodiment of the invention, the server is configured as a web portal to selectively allow access to such patient physiological data by designated third parties, such as physicians, clinicians, relatives and the patient themselves. In accordance with another important aspect of the invention, the system provides for enhanced functionality relative to known systems and allows trends of the physiological data to be selectively generated. In addition, any third party can set thresholds to automatically notify the patient or other third parties by various communication methods including e-mail and/or pager when a particular physiological characteristic exceeds a predetermined threshold. The system is also configured to provide reminders to patients to take readings.

DESCRIPTION OF THE DRAWINGS

These and other advantages of the present invention will be readily understood from the following specification and attached drawing wherein.

DETAILED DESCRIPTION

The present invention relates to a patient monitoring system for monitoring various physiological characteristics of a patient, such as blood pressure, pulse rate and others, as discussed below. The system includes a portable physiological transducer or patient monitoring device that can be worn by a patient in both single user and multi-user applications. The patient monitoring device is adapted to monitor physiological characteristic data of the patient and wirelessly transmit the data to a local hub or base station. In order to reduce the complexity of the system, the hub or base station is configured to automatically transfer the data to a remote server by way of a public or private communication network. In accordance with an important aspect of the invention, the system is configured to selectively enable access to a patients' physiological data by various selectable third party users, as well as the patient. In accordance with another aspect of the present invention, the patient monitoring system provides enhanced functionality relative to known systems. For example, the system in accordance with the present invention enables selectable third party users, as well as the patient, to monitor trends in the data for the physiological characteristics, as well as set alarms, which can automatically generate communications with the patient and/or third parties when a physiological characteristic exceeds a predetermined value. These communications can be, for example, by e-mail or pager. In one embodiment of the invention, a bi-directional communication link is provided between the patient monitoring device and the local hub. This bi-directional communication link allows communications to be sent to the patient monitoring device, for example, to remind a patient to take a physiological reading. The bi-directional communication link also allows handshaking between the patient monitoring device and the local hub to insure the transfer of physiological data to the local hub.

Figure 1:
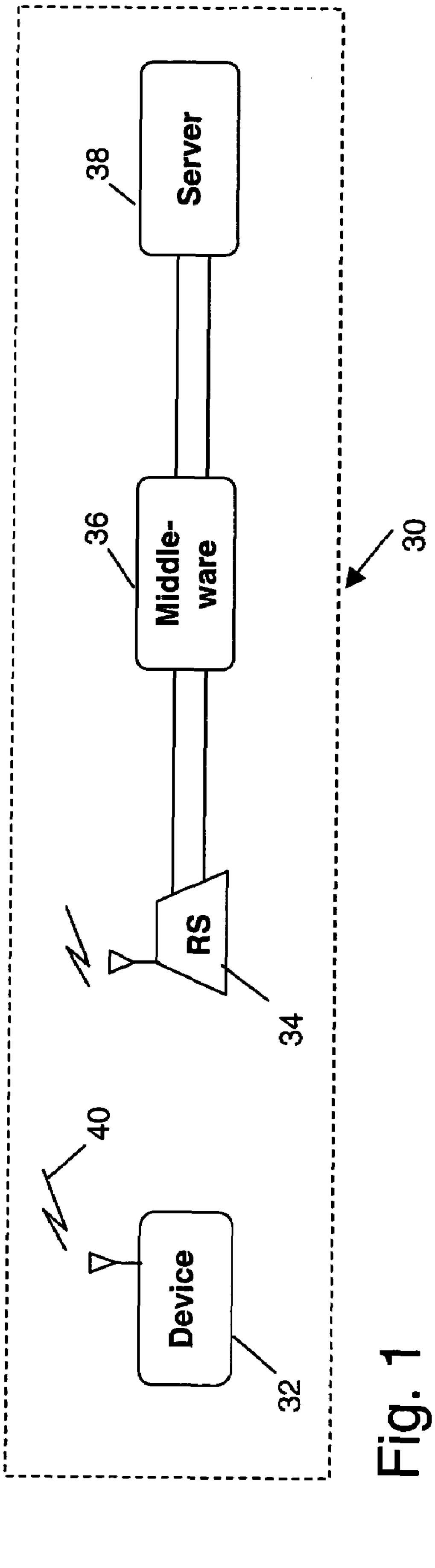
FIG. 1 is a block diagram of the patient monitoring system in accordance with the present invention.
Figure 2:
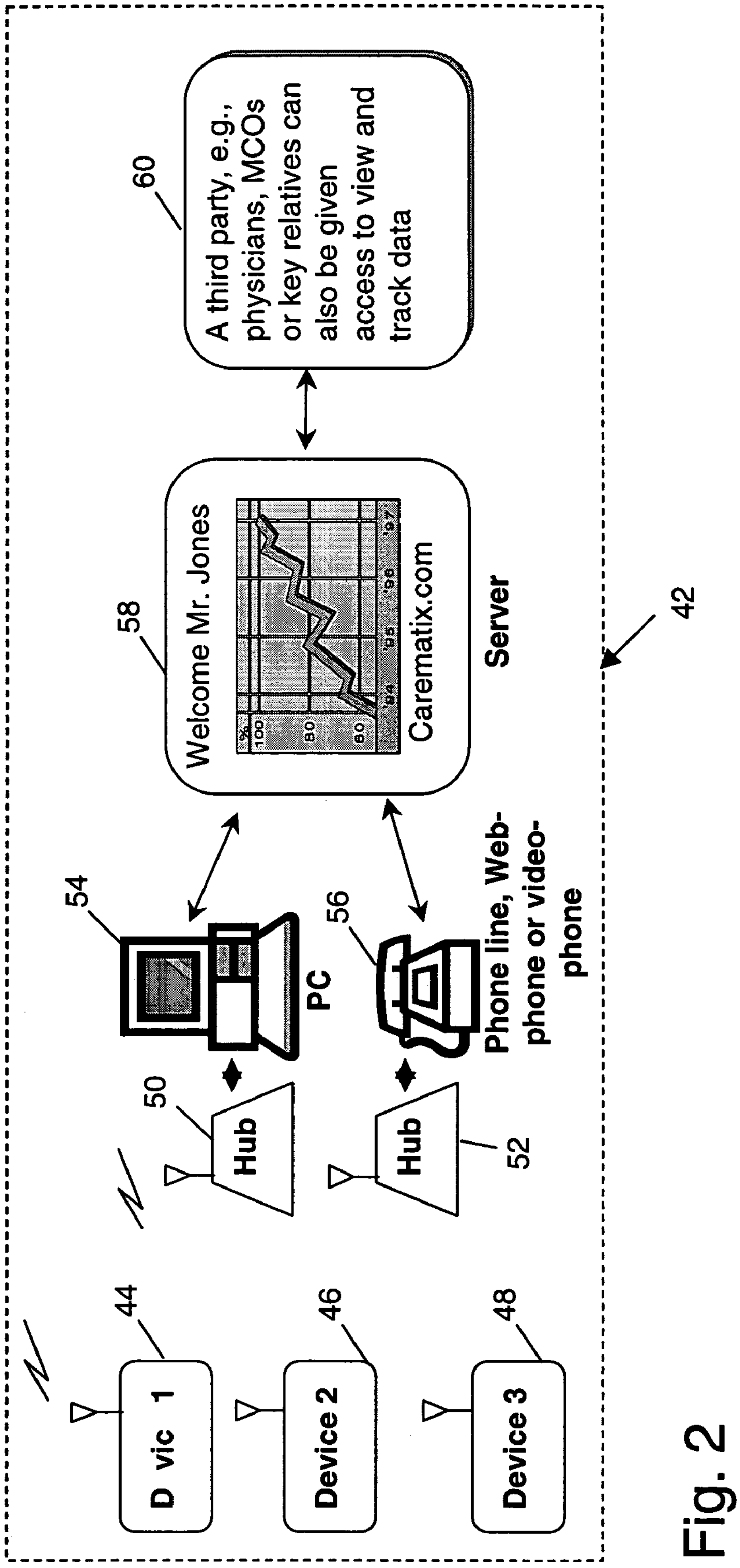
FIG. 2 is a block diagram of an alternate embodiment of the invention, illustrated in FIG. 1, illustrating the use of the invention in a multi-user, multi-hub environment.
Figure 3:
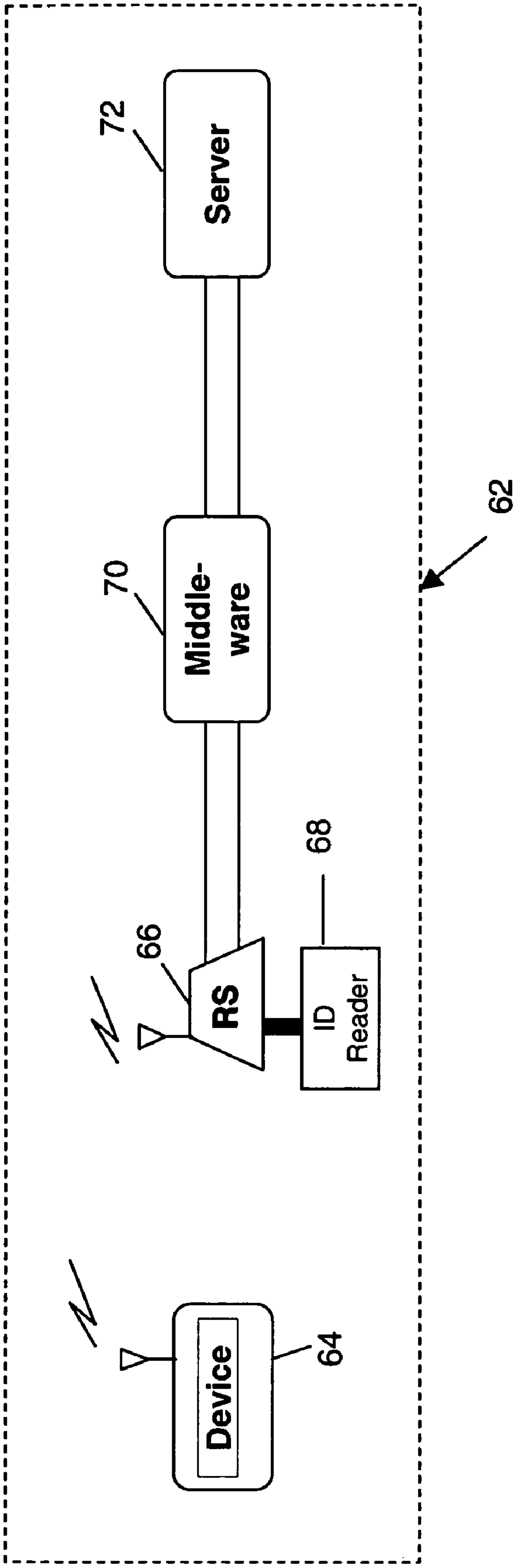
FIG. 3 is a block diagram of an alternate embodiment of the invention, illustrated in FIG. 1, for a multi-user environment, single hub environment.
Figure 4:
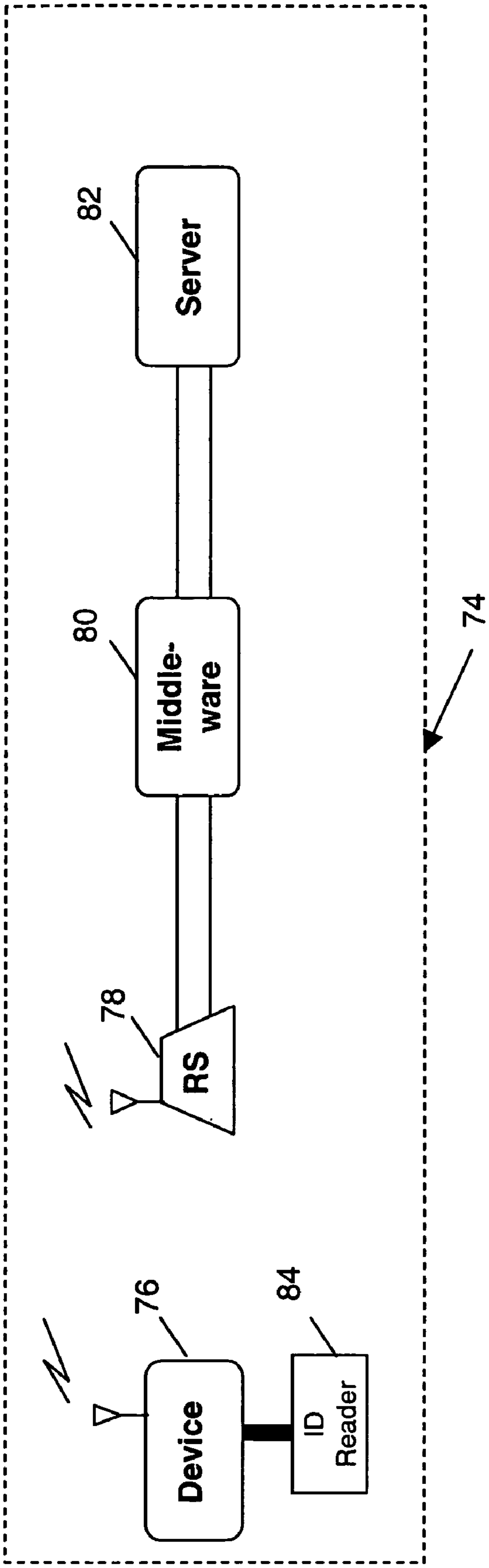
FIG. 4 is a block diagram of another alternate embodiment of the invention illustrated in FIG. 1 for a multi-user, single hub environment.

As will be discussed in more detail below, the system in accordance with the present invention can be utilized in a wide variety of applications. For example, FIG. 1 illustrates a single user/single hub application. FIG. 2 illustrates a multiple user/multiple hub application. FIGS. 3 and 4 illustrate a multiple user/single hub environment, for example, a cardiac rehabilitation facility in which each of the patients wear a portable heart monitor during cardiac rehabilitation.

Figure 5:
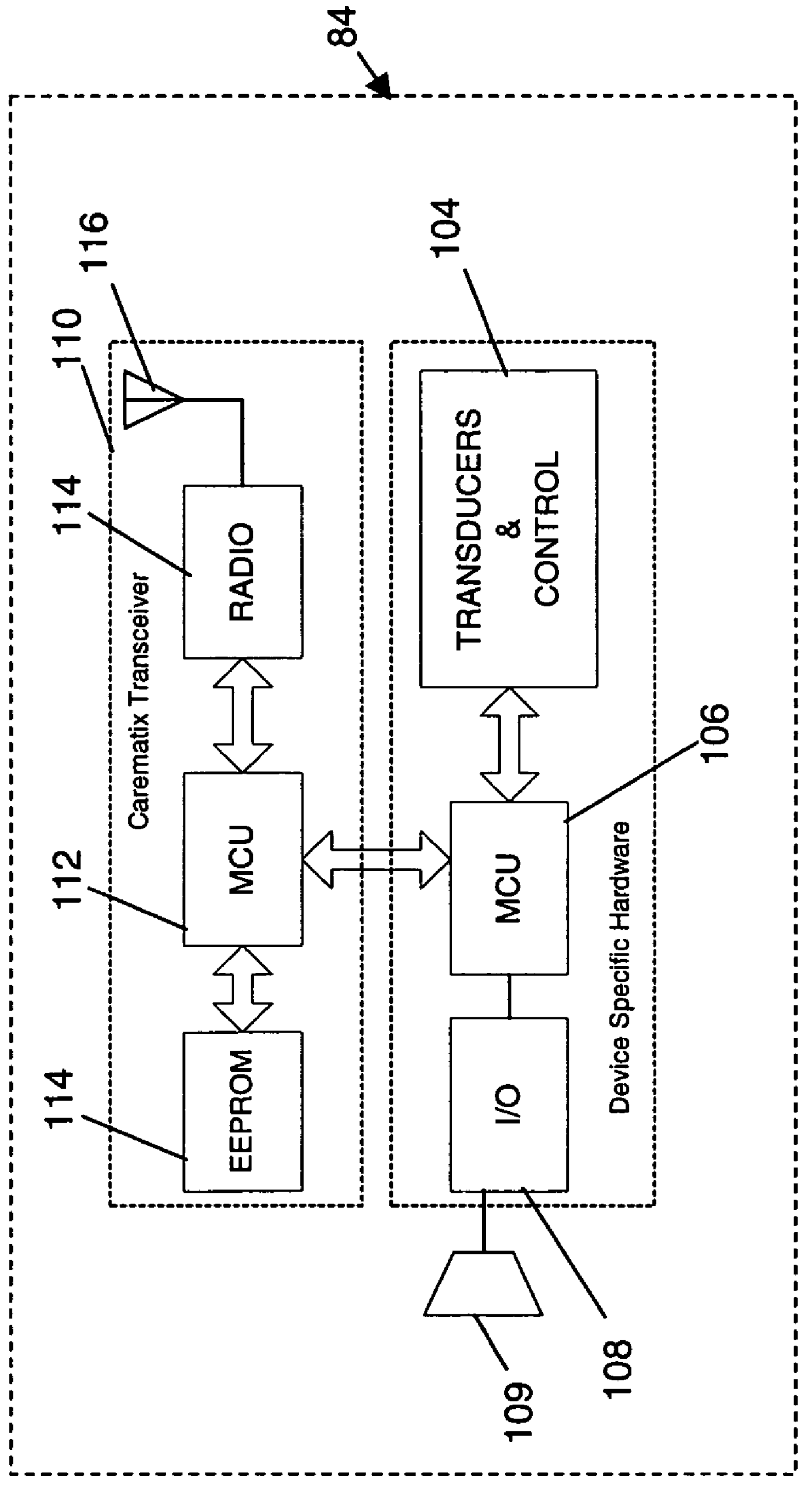
FIG. 5 is a block diagram of an exemplary physiological transducer for relatively complex transducers such as an electrocardiograph for use with the present invention.
Figure 6:
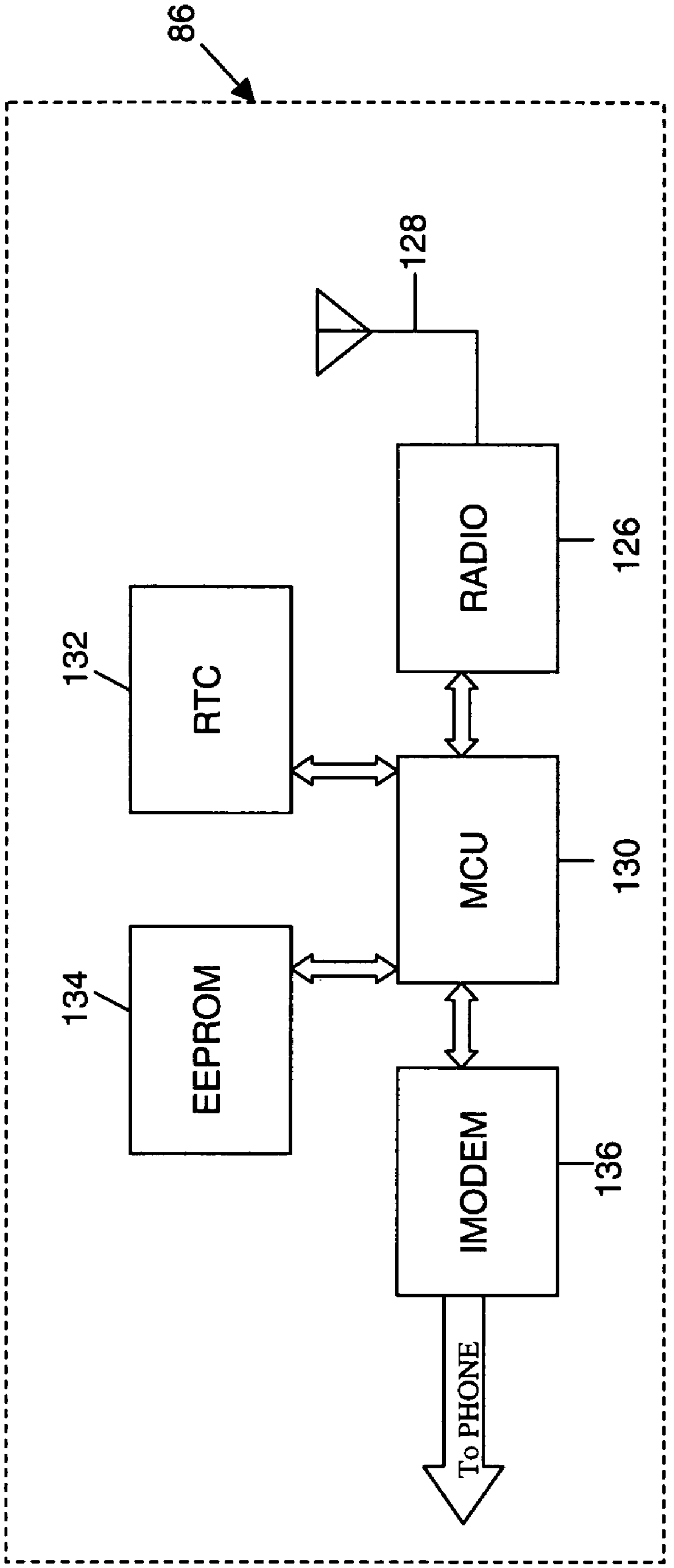
FIG. 6 is a block diagram of exemplary self contained hub or base station for use with the present invention.
Figure 7:
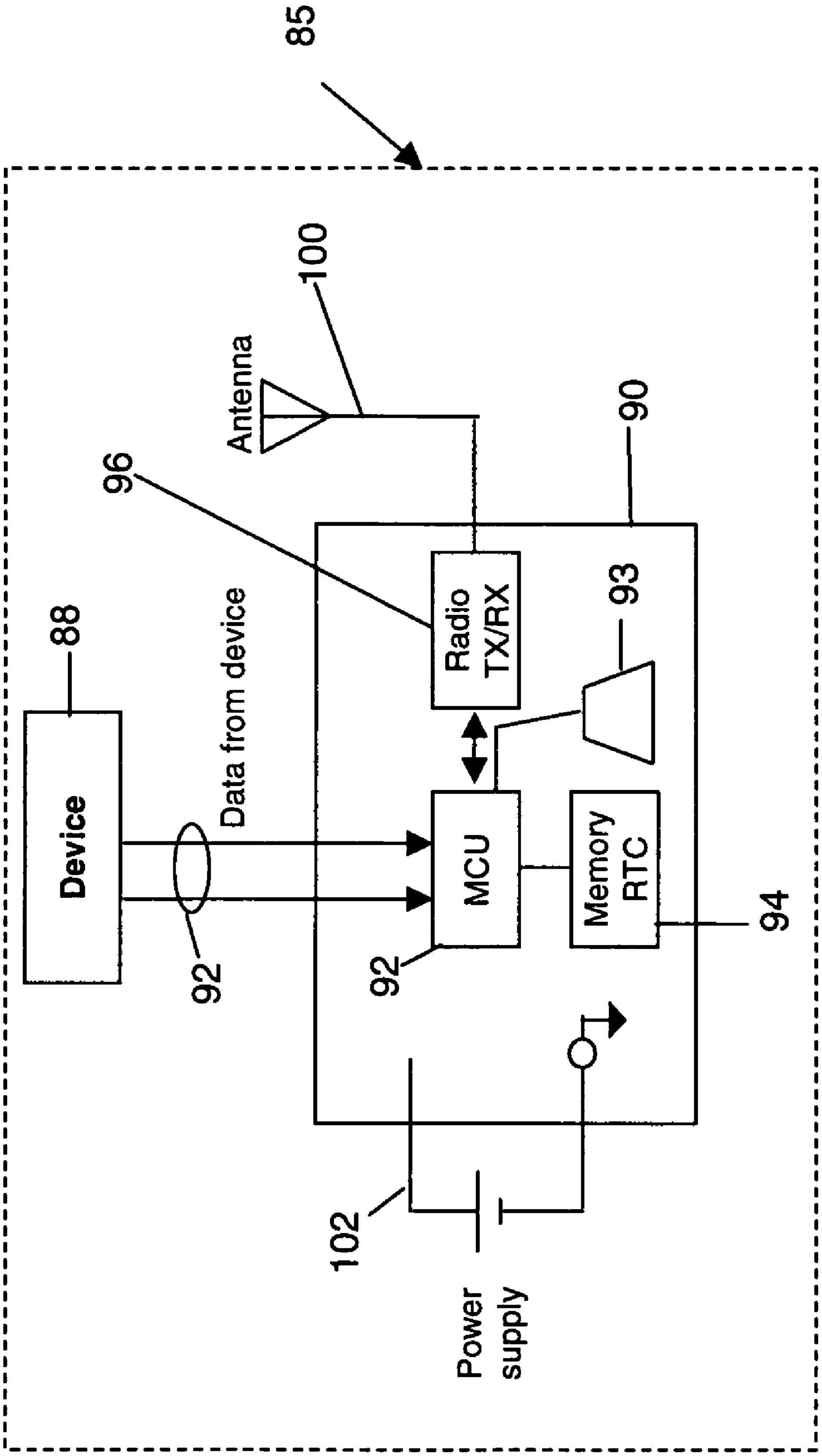
FIG. 7 is an exemplary schematic diagram of a relatively simple physiological transducer such as a blood pressure monitor, for use with the present invention.
Figure 8:
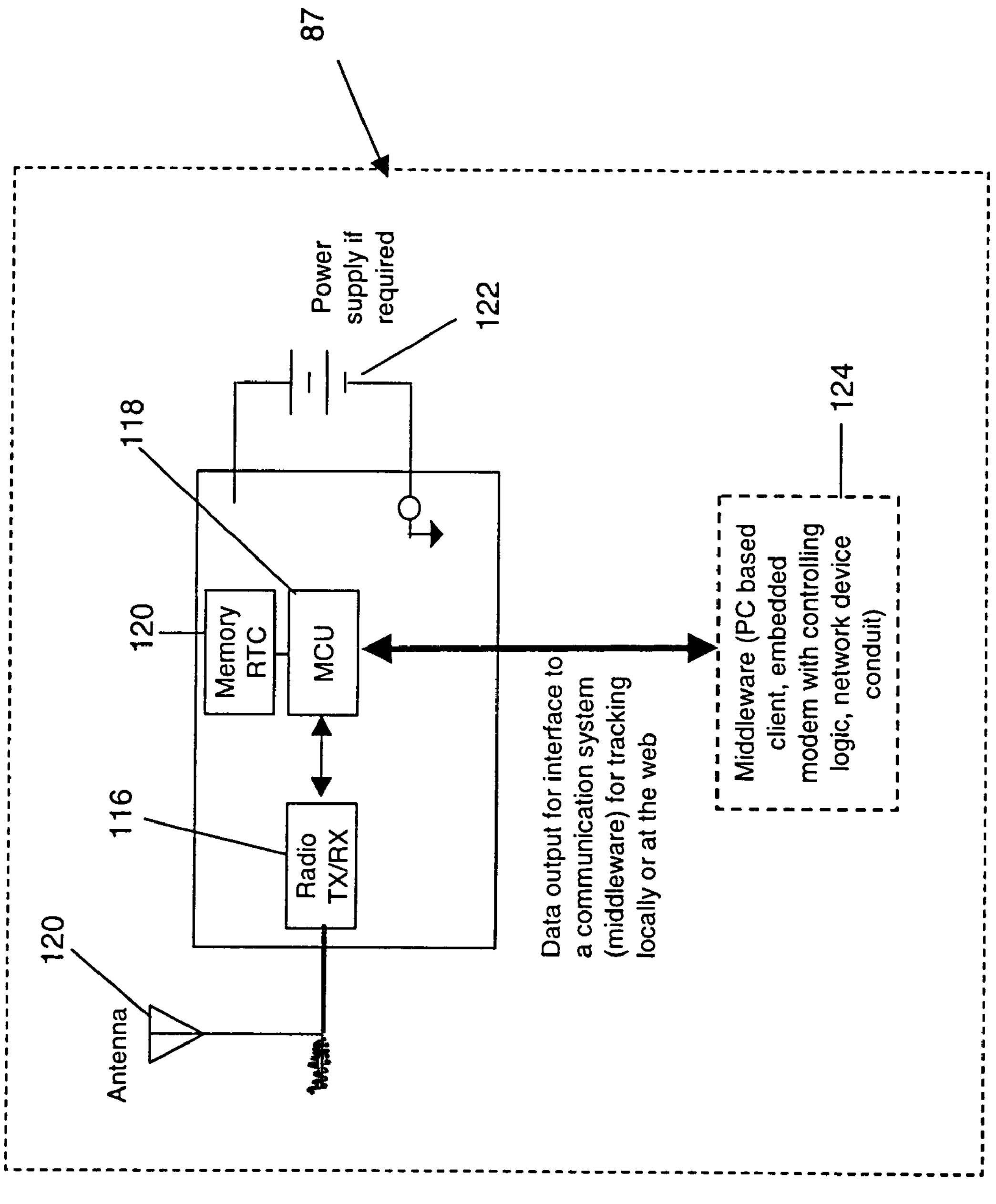
FIG. 8 is an exemplary schematic diagram of an alternative hub or base station that is adopted to be connected to a middleware device, for use with the present invention.
Figure 9A:
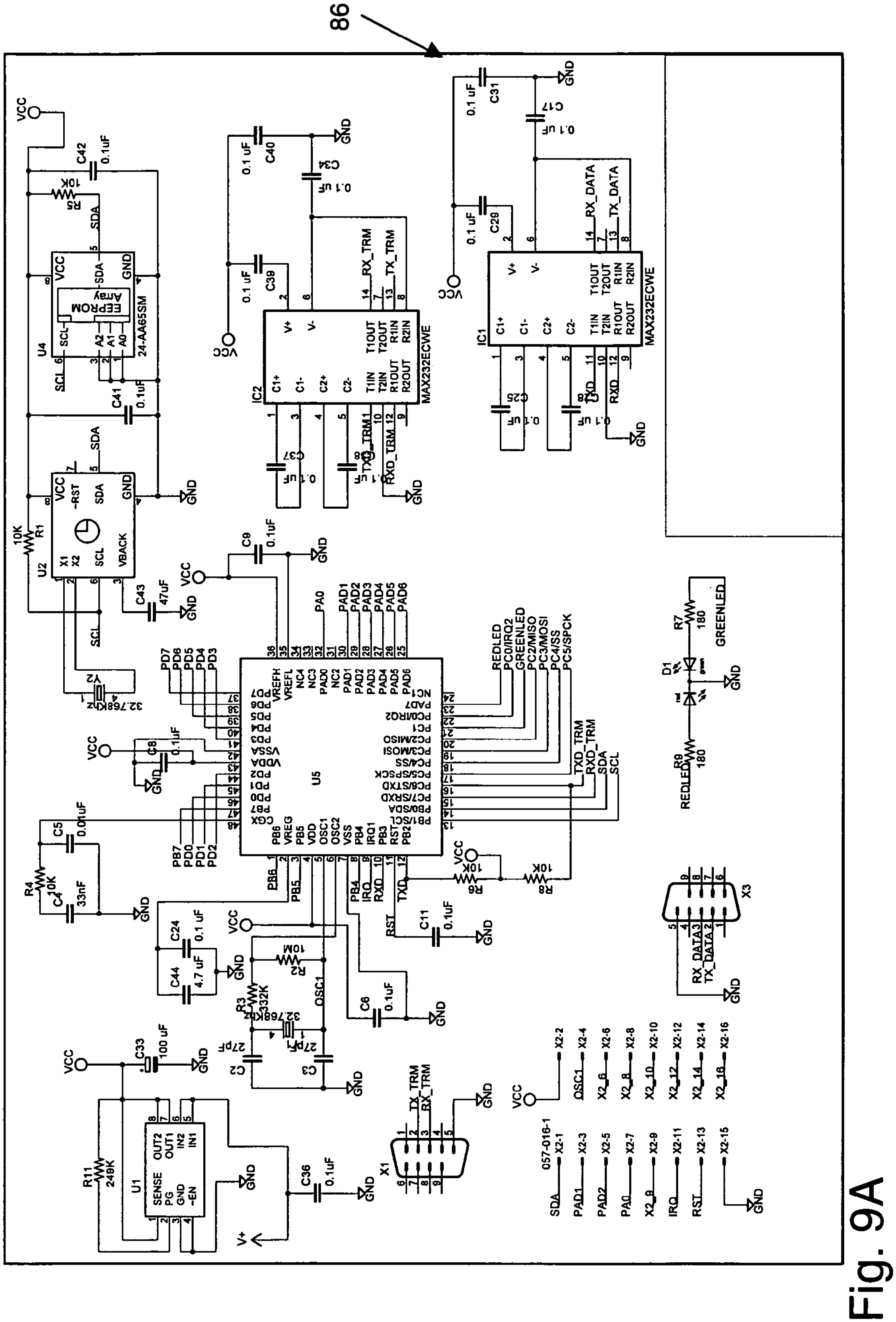
FIG. 9A is a schematic diagram of the hub illustrated in FIG. 6.
Figure 9B:
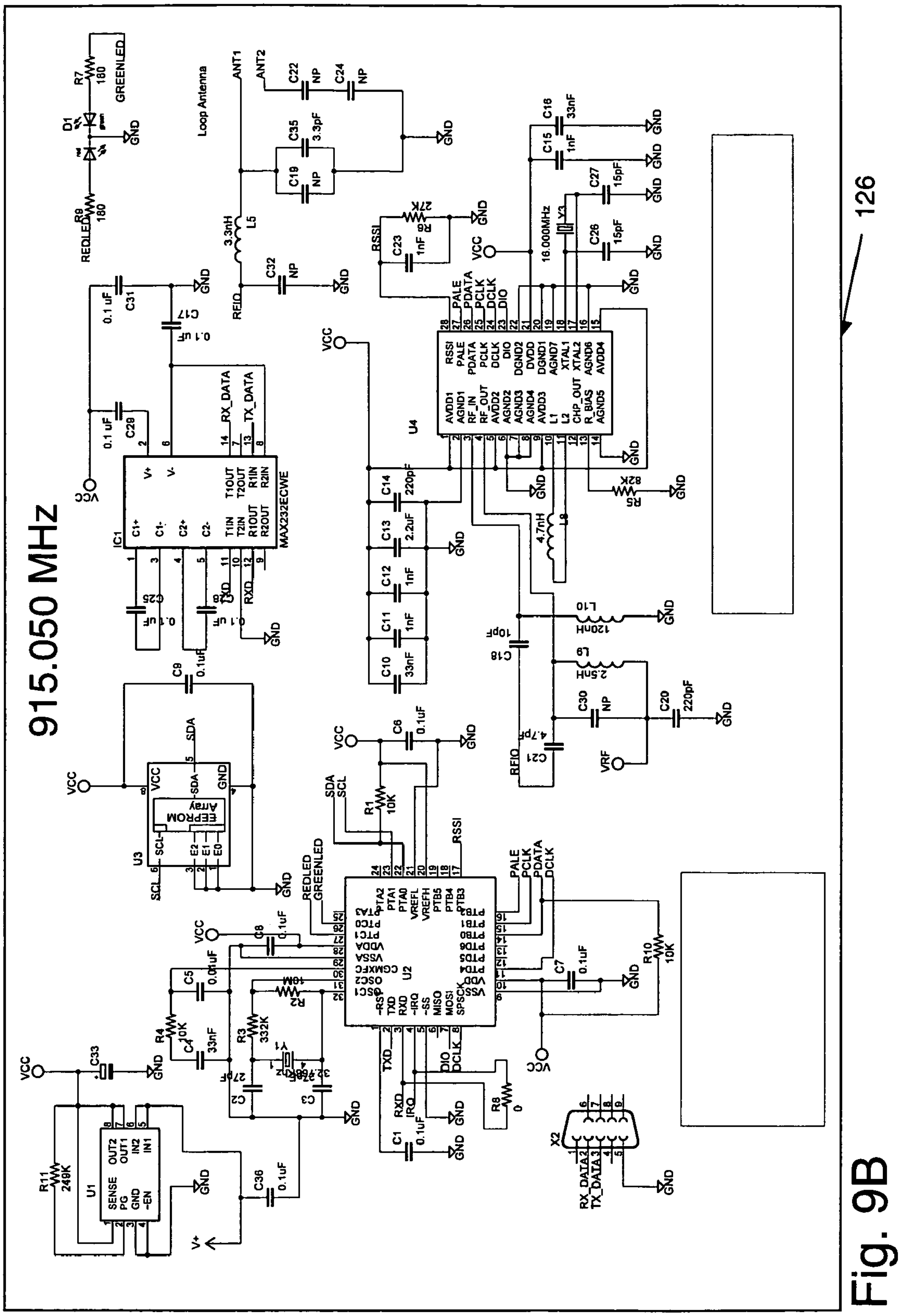
FIG. 9B is a schematic diagram of the transceiver incorporated into the hub illustrated in FIG. 9A.
Figure 10:
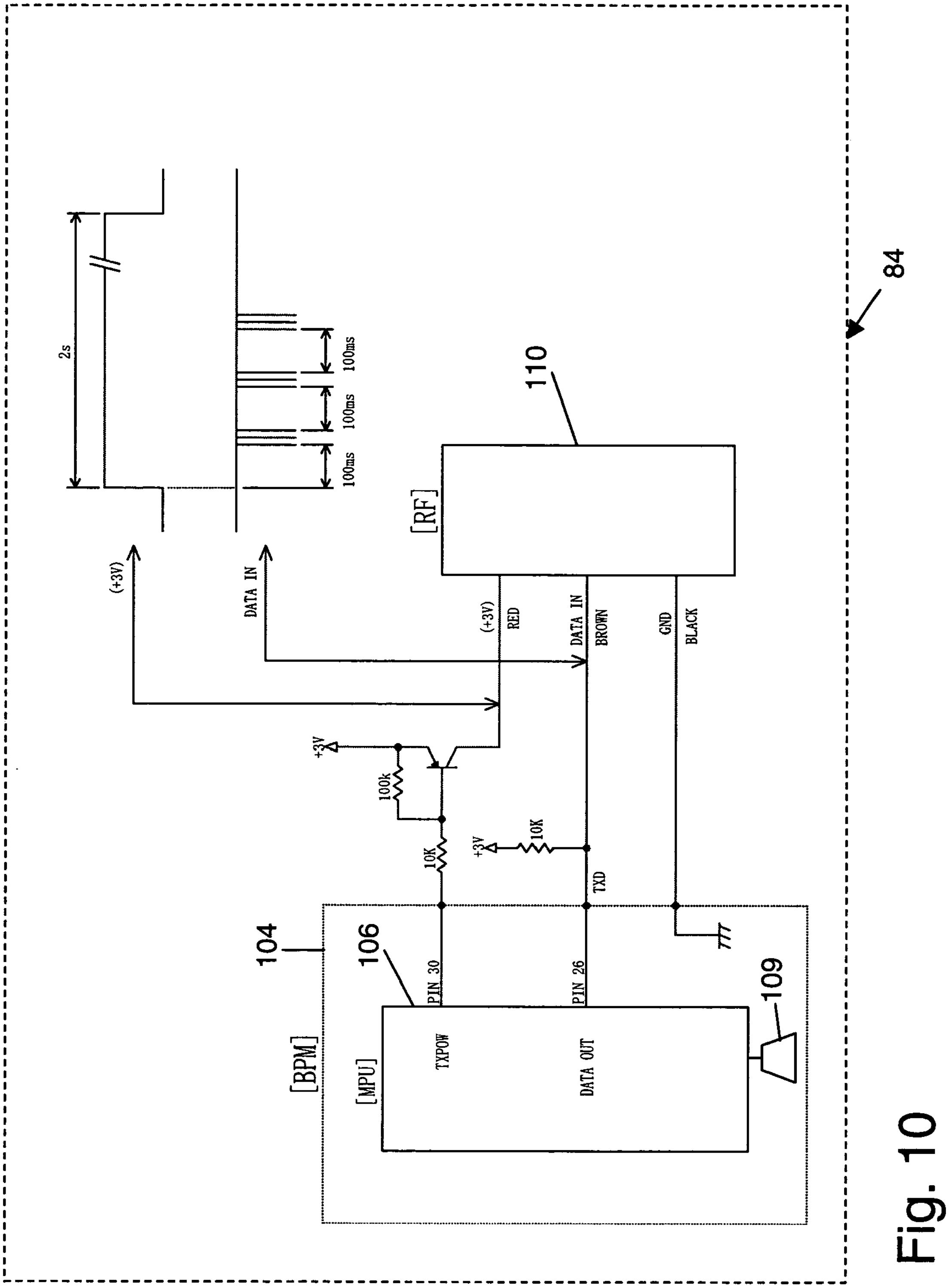
FIG. 10 is a schematic diagram of the exemplary physiological transducer illustrated in FIG. 7.

FIGS. 5-10 illustrate exemplary hardware diagrams for the portable physiological transducer and the hub for use with the present invention. In particular, FIG. 5 illustrates an exemplary block diagram of a portable physiological transducer for relatively complex transducers, such as a electrocardiograph. FIG. 7 illustrates an exemplary block diagram of a relatively simple portable physiological transducer, for example, a blood pressure transducer. Both transducers illustrated in FIGS. 5 and 7 may include an audio or visual indicating device to enable reminder messages to be sent to the patient monitoring device. FIG. 6 illustrates a block diagram of a exemplary self contained hub or base station for use with the present invention. FIG. 8 illustrates a block diagram of an exemplary hub that is adapted to be connected to a middleware device. FIG. 9A is a schematic diagram of a self contained hub illustrated in FIG. 6. FIG. 9B is a schematic diagram of the transceiver incorporated into the hub, illustrated in FIG. 9A. FIG. 10 illustrates an exemplary schematic diagram for a relatively simple patient monitoring device, such as a blood pressure monitor.

Figure 11:
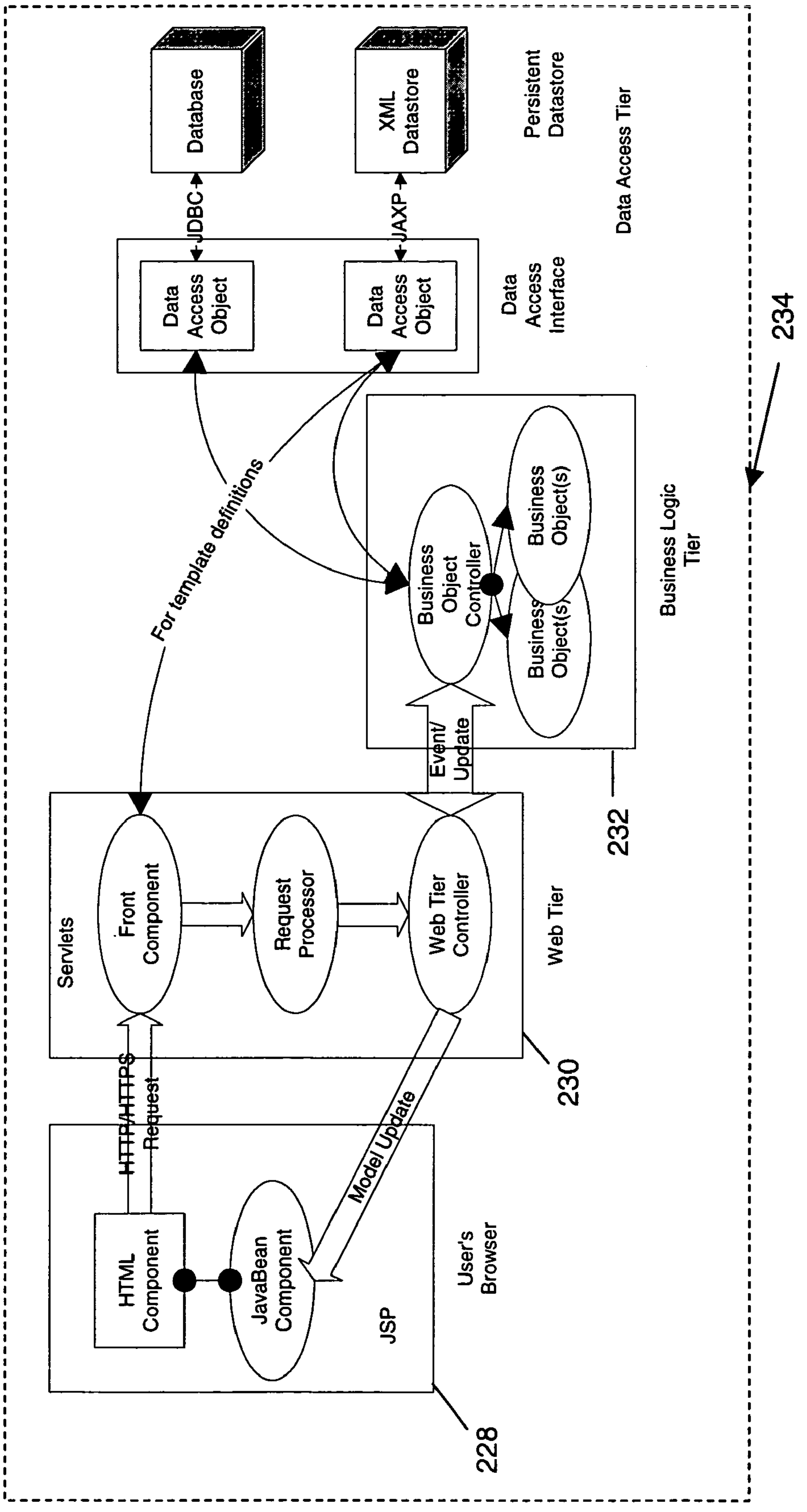
FIG. 11 is an exemplary block diagram of the server application architecture in accordance the present invention.
Figure 12:
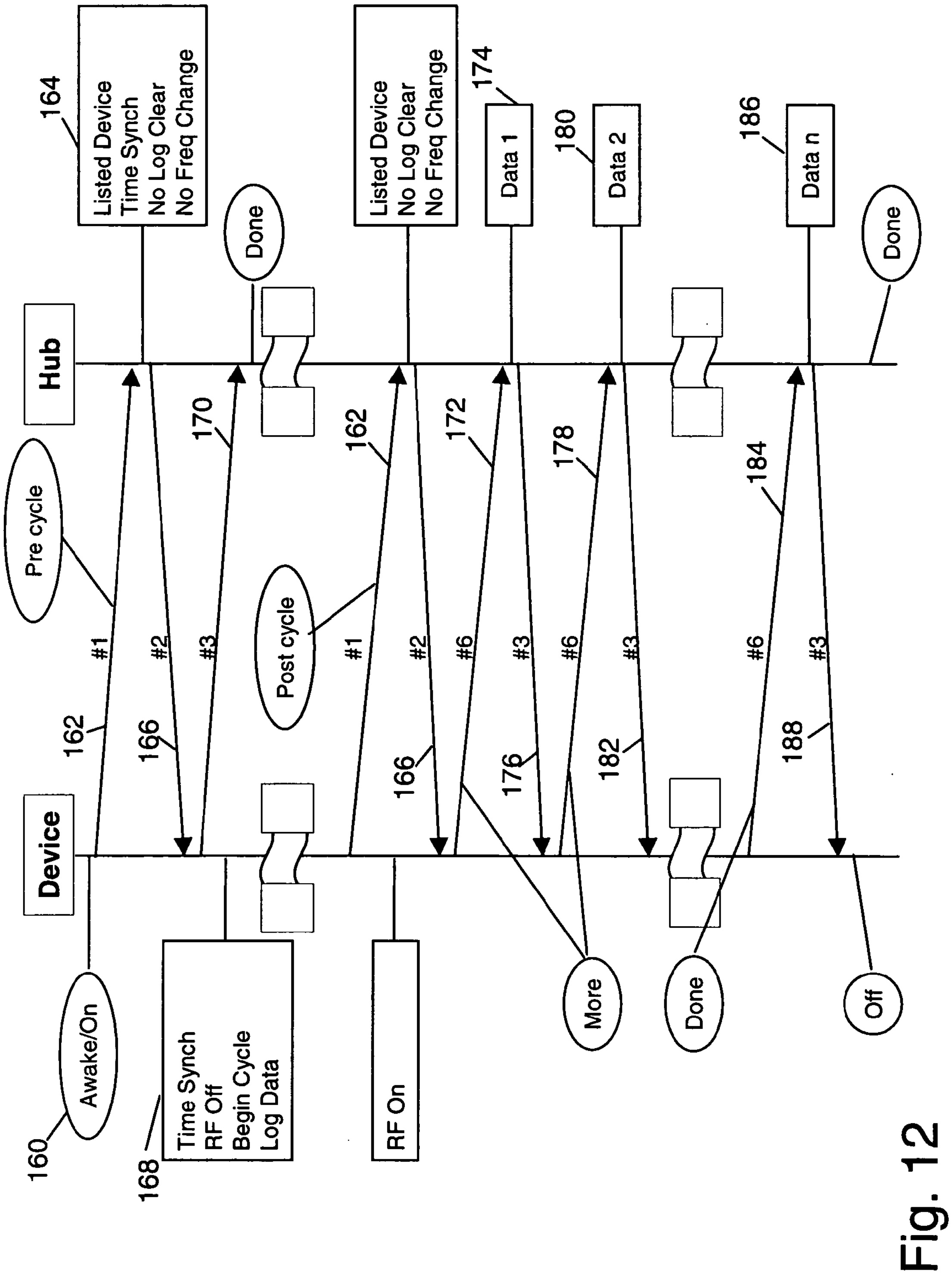
FIG. 12 is a diagram illustrating an exemplary message exchange between a patient monitoring device and a hub for the system in accordance with the present invention.
Figure 13:
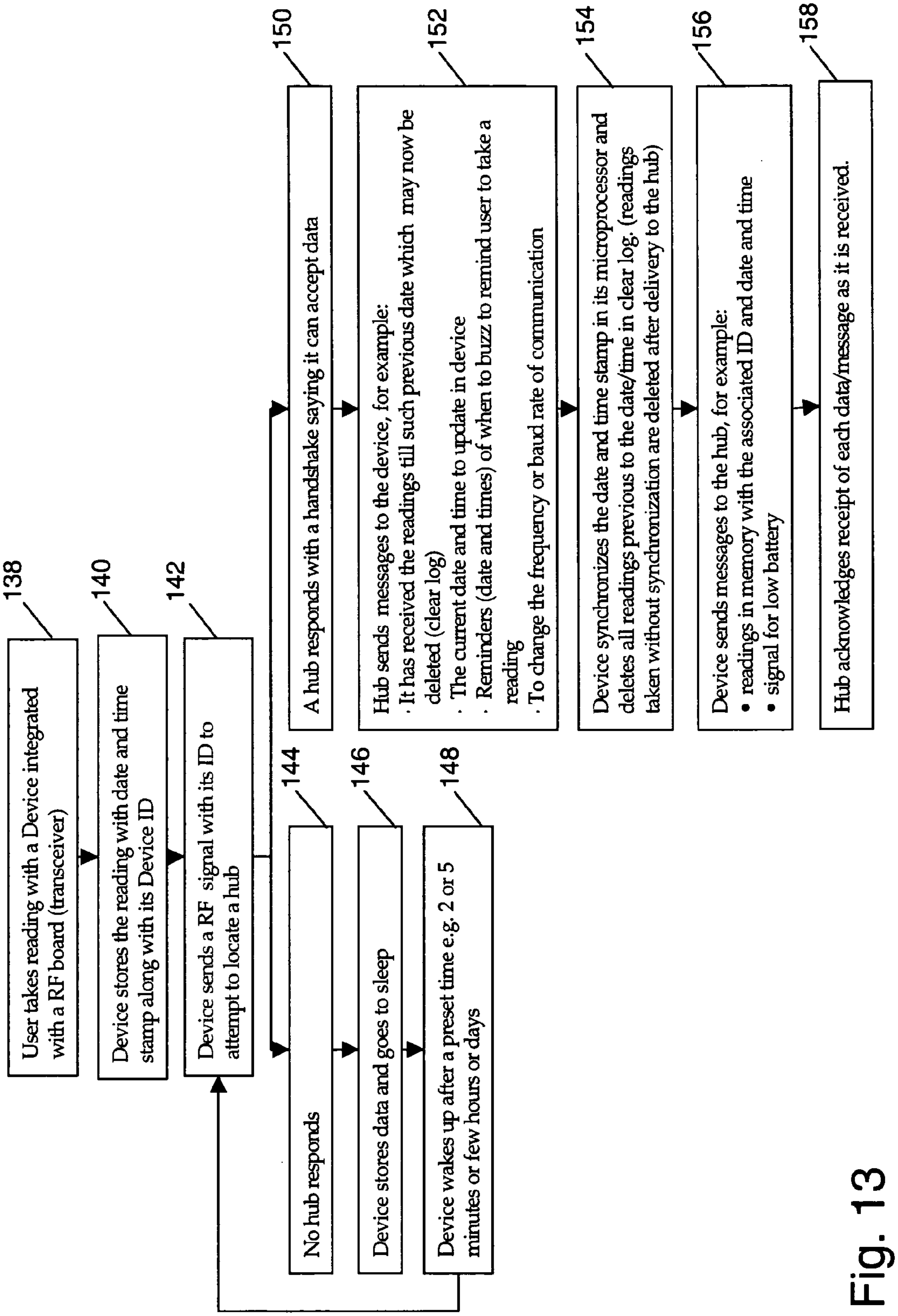
FIG. 13 is an exemplary software flow diagram for synchronizing the patient monitoring device to a hub in accordance with the present invention.
Figure 14:
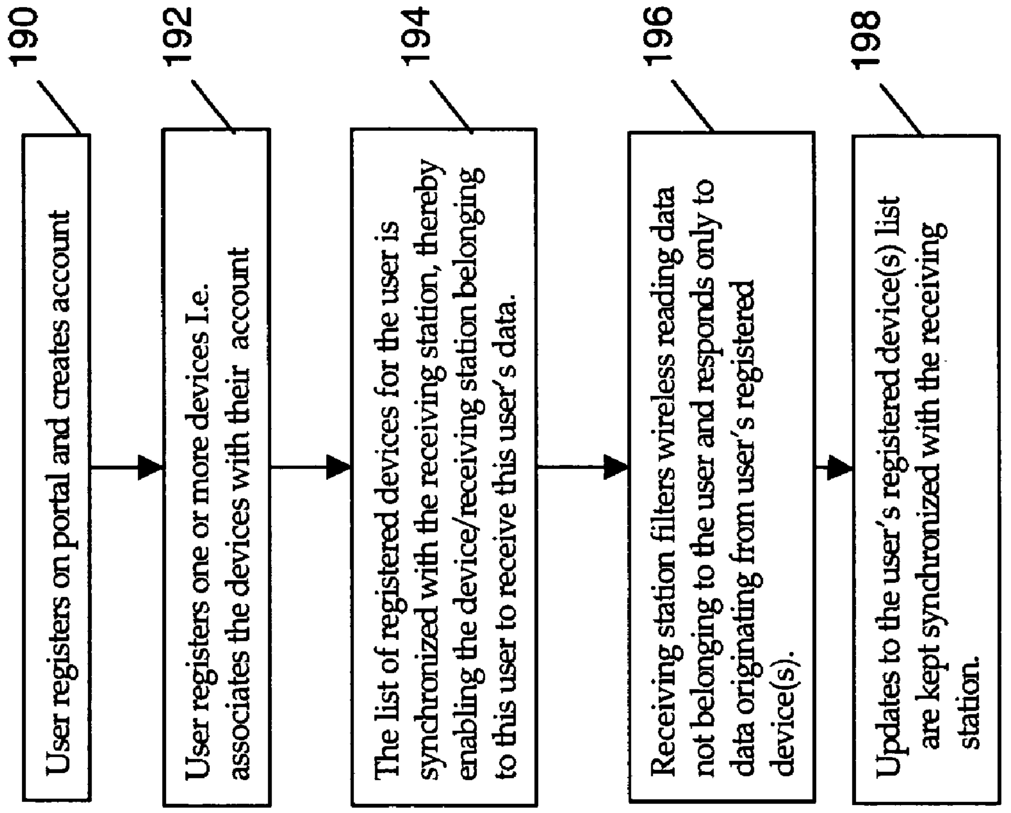
FIGS. 14 and 15 are exemplary flow diagrams illustrating the hub to web server synchronization.
Figure 15:
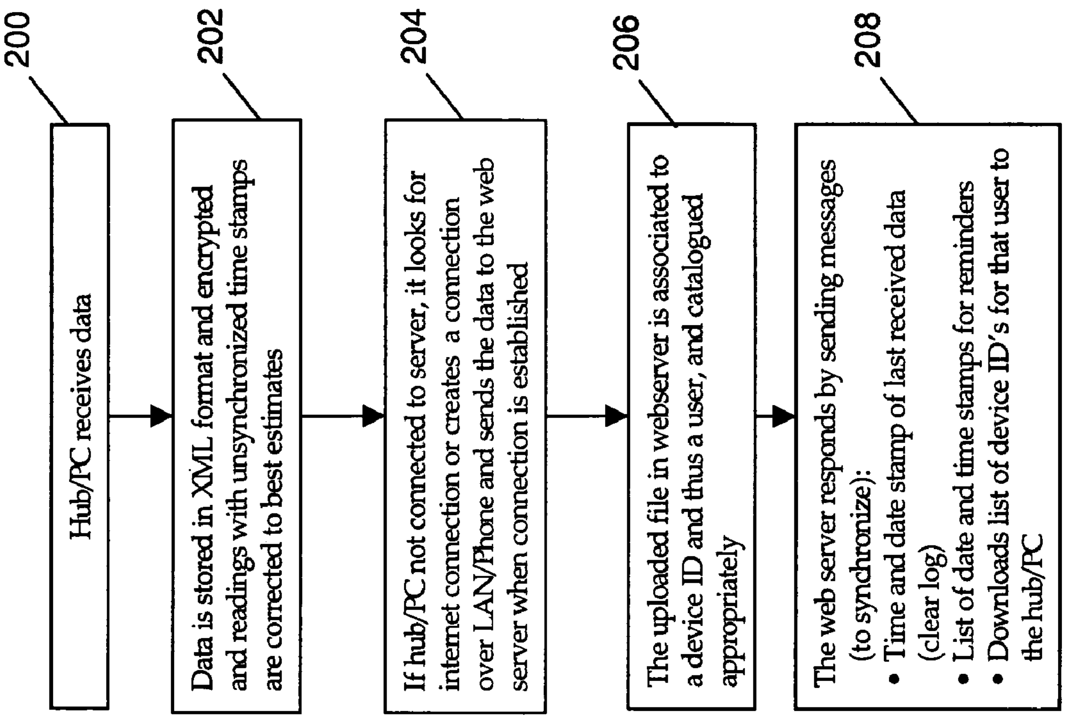
Figure 16:
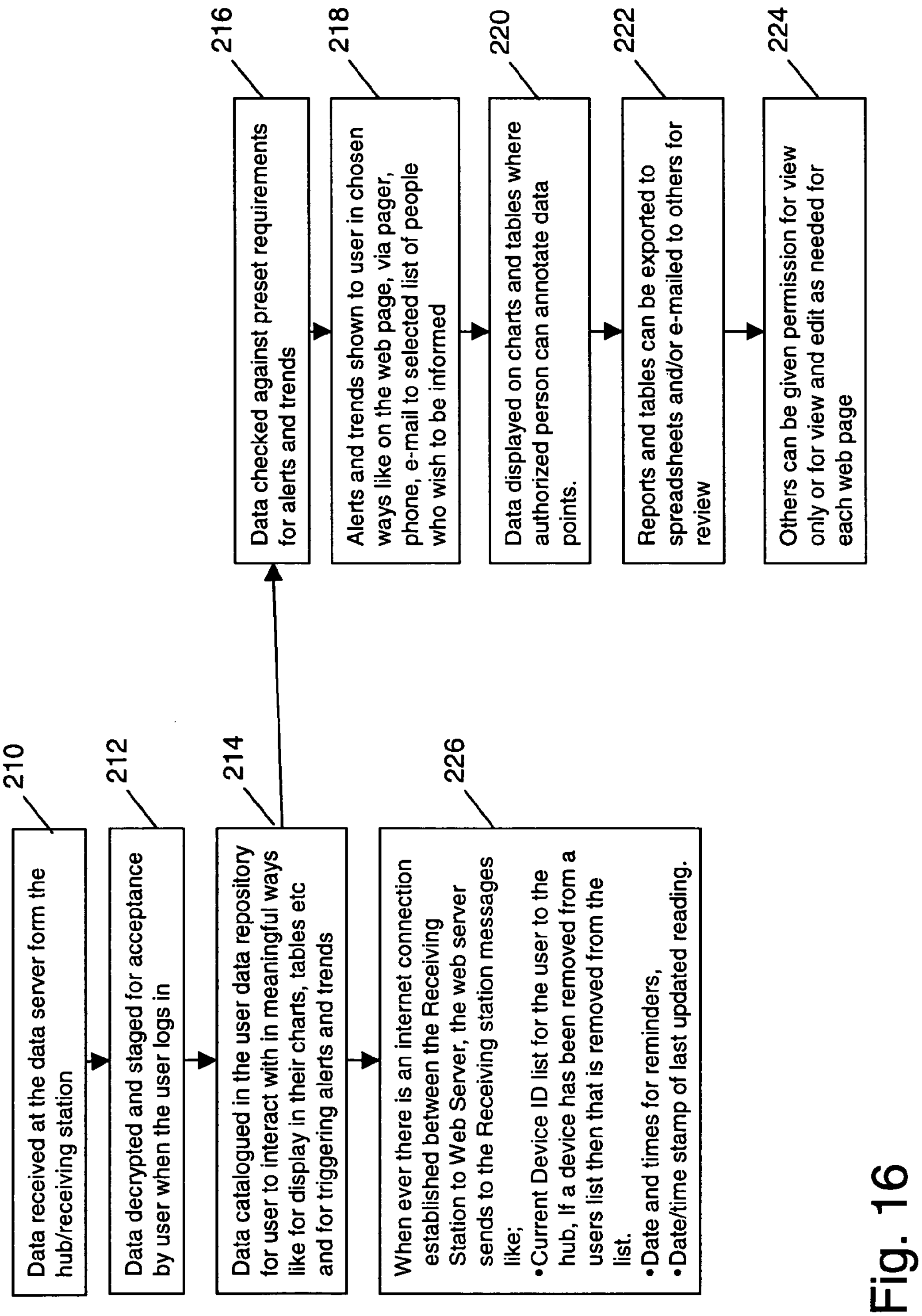
FIG. 16 is an exemplary flow diagram illustrating the data server/portal to user interaction in accordance with the present invention.

FIGS. 11-16 relate to the software. FIG. 11 is a block diagram of the server application architecture. FIG. 12 is an exemplary block diagram illustrating an exemplary message exchange between a portable physiological transducer or patient monitoring device and the self contained hub in accordance with the present invention. FIG. 13 is an exemplary software flow diagram illustrating the synchronization of the patient monitoring device with the hub in accordance with the present invention. FIGS. 14 and 15 illustrate the synchronization of the hub to the web server. FIG. 16 illustrates an exemplary flow diagram illustrating the data server to user interaction in accordance with the present invention.

In one exemplary embodiment of the invention, the system is configured as a web portal. In this embodiment, the server is configured as a web server and selectively allows third party access as well as access by the patient to the physiological data transmitted by the portable patient monitoring device. In addition, the system can be used to provide aural and/or visual signals to the patient monitoring device to remind a patient to take readings. As discussed above and as will be discussed in more detail below, various third parties, such as the physician and/or relatives, as well as the patient, can not only access the physiological data of the patient but also view trends of such data and also set alarms which automatically generate messages to either the patient and/or other third parties when the physiological characteristics of the patient exceed a preset value. In accordance with this embodiment, various screen shots as illustrated in FIGS. 17-23 are provided.

System

FIGS. 1-4 illustrate various system applications for the patient monitoring system in accordance with the present invention. In particular, single user/single hub applications, as well as multiple user/single hub and multiple user/multiple hub applications are within the broad scope of the present invention. As such, the patient monitoring system in accordance with the present invention can be used in a relatively wide variety of applications from non-clinical applications, such as a home healthcare and health club applications, as well as various clinical applications.

Referring first to FIG. 1, an embodiment of a patient monitoring system is illustrated and generally identified with the reference numeral 30. The patient monitoring system 30 illustrates a single user/single hub application, for example, a home healthcare application. In this application, the patient monitoring system 30 includes a portable physiological monitor or patient monitoring device, identified with the reference numeral 32, a local hub 34, a middleware device 36, which may or may not be incorporated into the hub 34, as well as a remote server 38. The patient monitoring device 32 can be one of multiple portable physiological transducer, such as a blood pressure monitor, heart rate monitor, weight scale, thermometer, spirometer, single or multiple lead electrocardiograph (ECG), a pulse oxymeter, a body fat monitor, a cholesterol monitor or a signal from an exercise machine, such as a heart rate. As will be discussed in more detail below, the patient monitoring device 32 is a portable device worn by the patient and includes a single or bi-directional wireless communication link, generally identified with the reference numeral 40, for transmitting data from the patient monitoring device 32 to the local hub or receiving station 34 by way of a wireless radio frequency (RF) link using a proprietary or non-proprietary protocol.

In this embodiment of the invention, the system includes a local hub or receiving station 34 which wirelessly receives data from the patient monitoring device 32 and automatically communicates it to a middleware device 36, which may be a personal computer, an Internet gateway, a home gateway, a phone, a video phone, or a phone modem. Alternatively, the middleware device 36 may not be required if the hub 34 includes its own processing equipment, as will be discussed below. In particular, the middleware device 36 may form part of the hub 34.

The hub or receiving station 34 may be a receiver or transceiver for receiving data from the patient monitoring device 32. Communication, if required, between the hub 34 and the middleware device 36, may be over various communication links, such as a direct connection, such a serial connection, USB connection, Firewire connection or may be optically based, such as infrared or wireless based, for example, home RF, IEEE standard 802.11a/b, Bluetooth or the like.

The middleware device 36 transfers the data received by the hub or receiving station 34 to a remote server 38. The communication link between the middleware device 36 and the remote server may be by direct connection, such as a serial connection, USB, Firewire or optically based such as infrared or wireless based such as home RF, IEEE standard 802.11b, Bluetooth or others. For longer distances, a communication link between the middleware device 36 and a remote server 38 may be by DSL, T-1 connection over a private communication network or a public information network, such as the Internet.

In accordance with one aspect of the invention, the remote server 38 may be configured to provide third party access to the patient physiological data forming a portal. The portal, for example, a web portal, allows the patient and/or third party users, such as relatives and physicians, to interact with the patient data in various ways as discussed below.

FIG. 2 illustrates a multi-user/multi-hub application of the present invention, generally identified with the reference numeral 42. In this embodiment, three (3) exemplary patient monitoring devices 44, 46 and 48 are used to transmit data to multiple hubs 50 and 52. The hubs 50 and 52 transfer the data to middleware devices 54 and 56, which, as discussed above may be a personal computer (PC) 54 or a phone line, web phone or video phone 56 or may be integrated into the hubs 50 and 52. In this embodiment, the middleware devices 54 and 56, in turn, transmit the data to a remote server 58. In accordance with an important aspect of the invention, various third parties, such as a physician or relatives, can selectively access the patient physiological data in the server 58, as indicated by the function block 60.

FIGS. 3 and 4 illustrate a multi-user/single hub application, for use in multiple user applications, such as a retirement home. Two embodiments of this application are contemplated as illustrated in FIGS. 3 and 4. Referring first to FIG. 3, the patient monitoring system is generally identified with the reference numeral 62. The patient monitoring system 62 includes a patient monitoring device 64, a hub 66, an ID reader 68, a middleware device 70 and a remote server 72. The patient monitoring device 64, hub 66, middleware device 70 and the server 72, as well as the communication links therebetween, are as described above. In the exemplary application illustrated in FIG. 3, the ID reader 68 is operatively connected to the hub 66 to accommodate different users in a multiple user environment. In such an application, each user is given a unique ID. This ID is input into the hub 66. Various types of identification are contemplated. For example, the ID reader 68 may be a swipe card, RF tag or push button. In this embodiment, the user ID is read from the ID tag of the user at the same time physiological data is being read from the patient monitoring device 64.

FIG. 4 illustrates an alternative embodiment of the invention illustrated in FIG. 3. This embodiment is generally identified with the reference numeral 74. The patient monitoring system 74 includes a patient monitoring device 76, a hub 78, a server 82 and an ID reader 84. The patient monitoring system 74 is similar to the patient monitoring system 62, illustrated in FIG. 3, except that the patient monitoring system 74 is configured such that the ID reader 84 is coupled to the patient monitoring device 76. In this embodiment, the user ID and physiological data is transmitted together to the hub 78. In lieu of the ID reader, the patient monitoring device 76 can be configured such that the device transmits an unique ID with the physiological data. Thus, different users wearing different devices can easily be correlated by the system.

Hardware

The hardware for the patient monitoring device, as well as the hub, is illustrated in FIGS. 5-10. As mentioned above, FIGS. 5 and 7 relate to a patient monitoring devices, generally identified with the reference numerals 84 and 85, for use with the present invention. FIGS. 6 and 8 illustrate exemplary hubs for use with the present invention. FIG. 10 is an exemplary schematic diagram of the patient monitoring device 84, illustrated in FIG. 5.

Exemplary Patient Monitoring Devices

Various embodiments of the patient monitoring devices 84 and 85 are contemplated. Both embodiments may optionally include a visual or audio indicating device to allow visual and/or audio communications to be sent from the system to the patient monitoring device. The patient monitoring device 85 (FIG. 7) is representative of patient monitoring devices which utilize relatively simple transducers, such as a blood pressure monitor, heart rate monitor and others. The patient monitoring device 85 includes a transducer 88, such as a blood pressure transducer, coupled to a communication module 90. The communication module 90 may include a microprocessor 92, a memory real time clock 94, as well as a transmitter for unidirectional communications or a transceiver 96 which enables bi-directional communication between the patient monitoring device 85 and a local hub, as discussed above. An audio or visual indicating device 93 may also be provided to enable alerts or messages to be sent to the patient monitoring device 85. The transducer 88 may be directly wired to the communication module 90, as indicated by the electrical leads 98. An antenna 100 is provided in order to provide a wireless link to the local hub, as discussed above. A power supply 102, such as a battery may be provided.

The MCU 92 may be, for example, Motorola model number 68HC908GP32. The radio 96 may be, for example, a Xemics model number XE 1201. The memory 94 may be, for example, an Atmelmodel number CAT 24AA65. The real time clock may be a Dallas Semiconductor model number DS 1675.

More sophisticated patient monitoring devices 84, as illustrated in FIG. 5, such as electrocardiograph (ECG) devices, may include one or more transducers which directly communicate with a microprocessor 106. An input/output (I/O) device 108 may be directly coupled to the microprocessor 106, for example, for receiving data from electrodes attached to the patients' body by way of electrical leads (not shown). As is well known in the art, this data is received by the microprocessor 106 and configured by the transducer 104 and communicated to a communication module 110. The communication module 110 includes its own microprocessor 112, a memory 114 such as an electrically erasable programmable read only memory (EEPROM), a radio 114 for bi-directional communication or simply a transmitter for unidirectional communication, as well as an antenna 116.

Various physiological transducers can be integrated into the system. These transducers are similar to various commercially available transducers such as: a blood pressure transducer, such as A&D blood pressure cuff, model number UA-767PC; a weight scale, such as an A&D scale, model number UC-321; a blood glucose meter, such as a LifeScan ONE TOUCH® Ultra; a pulse oximeter, such as a PalmSat Model 2500; a spirometer, such as a Micro Direct model MICRO DL; a prothromben time test for Coumadin® therapy, such as a PT/NR Protime Microcoagulation System; and a cholesterol monitor, such as a LSP 3101 Personal Cholesterol Monitor Kit. Virtually any physiological transducer which generates an electrical signal can be implemented in the system.

Hub Hardware

Exemplary block diagrams for the hub for use with the present invention is illustrated in FIGS. 6 and 8. Referring first to FIG. 8, the hub 87 includes a radio 116, a microprocessor 118 and a memory/real time clock 120. The hub 87 also includes and an antenna 120 and a power supply 122 if required. This embodiment of the hub 87 is for an embodiment in which there is a separate communication link as discussed above to a middleware device 122 for embodiments in which the middleware device 122 is separated from the hub 87.

FIG. 6 illustrates an alternative embodiment of the hub, identified with the reference numeral 86 in which the middleware device is integrally formed with the hub. In this embodiment, the hub 86 includes a radio 126 and an antenna 128 for receiving data, wirelessly from the patient monitoring device. The hub 86 also includes a microprocessor 130, a real time clock 132, a memory device such as a EEPROM 134 and a modem 136. The microprocessor 130, radio 126, real time clock 132 and memory 134 may be as discussed above. The modem may be a ConnectOne embedded iModem, Model Number iM336UC-EM.

FIG. 9A is an exemplary schematic diagram of the hub 86 illustrated in FIG. 6. FIG. 9B is an exemplary schematic diagram of the transceiver 126 illustrated in FIG. 9A.

Software

FIGS. 11-16 illustrate the system software. FIG. 11 illustrates the server application architecture. FIG. 12 illustrates the message exchange between a patient monitoring device and the hub. FIG. 13 illustrates the software for synchronizing data from the patient monitoring device to the hub. FIG. 14 illustrates the synchronization between the hub and the remote server and specifically relates to user registration. FIG. 15 illustrates the software flow diagram for interaction between the hub and the web server. FIG. 16 illustrates the software flow diagram for interaction between the user and data server/portal.

Referring first to FIGS. 13-16, FIG. 13 illustrates the software for controlling the patient monitoring device and transmitting the data from the patient monitoring device to the hub. Initially, in step 138, on power up, the patient monitoring device, either on its own or in response to patient input, begins taking readings of a patient physiological characteristic. These readings are stored in the patient monitoring device along with a time stamp and device ID in step 140. In step 142, the patient monitoring device sends out RF signals with its ID in an attempt to locate a local hub. If no hub responds as indicated in step 144, the patient monitoring device stores the data and goes to sleep in step 146. Subsequently, after a preset time, the device awakens in step 148 and returns to step 142 and attempts to locate a hub.

Once a hub is located, the hub responds with a handshake signal indicating that it is available to receive data as indicated in step 150. After the handshake, the hub may communicate various information to the patient monitoring device in step 152. For example, the hub may send a message to the patient monitoring device indicating that previous readings have been received. The hub may also send a message to the patient monitoring device with the current date and time to update that device. In addition, the hub may send reminders at specified dates and times to remind a patient when to take readings for those patient physiological devices which do not constantly take readings. Finally, the hub may also send a message to the patient monitoring device to change the frequency or baud rate of the communication. Subsequently, in step 154, the patient monitoring device synchronizes its date and time stamp and deletes all previous readings to the date and time in order to initialize the patient monitoring device. After the patient monitoring device is initialized in step 154, the patient monitoring device then sends the data to the hub in step 156 with its associated ID and date and time. The patient monitoring device may also send data to the hub indicating that its battery is low. In step 158, the hub acknowledges receipt of each message received.

The message exchange between the patient monitoring device and the hub is illustrated diagrammatically in FIG. 12. Initially, as indicated in box 160, the patient monitoring device on power up sends a query to the hub, as indicated by the message 162. The hub in response to that query checks whether the ID number for the patient monitoring device is listed, as indicated by the block 164. In addition, the hub may also communicate its local date and time as well as control information with respect to clearing the log and frequency change, as message 164. This information is acknowledged and acted upon by the patient monitoring device, as indicated by the message 168. After the patient monitoring device is time synchronized with the hub, the patient monitoring device begins sending data to the hub along with its ID and time stamp, as indicated by the message 170.

The above message exchange may be identified as a pre-cycle message exchange. Such a pre-cycle message exchange is identified as a time period when the patient monitoring transducer is not actively recording data such as during a time period when a blood pressure cuff has not been inflated.

After the data has been transmitted from the patient monitoring device to the hub, post cycle messages include repeating the messages 162 and 166 after each data cycle has been completed. In addition, a message 172 may be sent from the patient monitoring device to the hub for the first piece of data, indicated by the box 174. After the hub receives the data 174, it sends a message back to the patient monitoring device indicating that the data 174 has been received. Once the patient monitoring device acknowledges from the hub that the first bit of data has been received, additional data is sent by way of a message 178 to the hub, as indicated by the data block 180. The hub responds that the data 180 was received by way of a message 182 back to the patient monitoring device. After all of the data has been transmitted from the patient monitoring device to the hub, the patient monitoring device sends a message 184 indicating that the next bit of data is the last bit of data in the memory to be sent by the patient monitoring device by way of the message 184. The hub then acknowledges receiving the last bit of data 186 by acknowledging by way of message 188 back to the patient monitoring device 188 that it has received that data 186.

FIGS. 14 and 15 illustrate the synchronization between the hub and the remote server. In accordance with an important aspect of the invention, the server in this embodiment is configured as a portal, for example, a web portal, which enables third party users to selectively access patient physiological data transferred to the remote server. In this application, users register on the portal and create an account in step 190. In step 192, the user registers one or more devices (i.e. device ID's) with their account. Next, in step 194, the list of registered devices for a particular user is synchronized with the hub thereby enabling the hub to receive data for the specified device IDs. In step 196, the hub filters wireless communications from various patient monitor devices and only responds to data originating from registered devices. In step 198, any updates of the registered devices with respect to a user's account are synchronized with the hub.

FIG. 15 illustrates a software diagram for transferring data between the hub and the remote server. Initially, in step 200, data is received by the hub as discussed above. In step 202, the data may be stored, for example, in XML format, for example, and optionally encrypted with readings with unsynchronized time stamps, which may be corrected to best estimates. In step 204, if the hub is not connected to the server, the server looks for an Internet connection or creates a connection over a LAN/phone line automatically and sends the data to the web server when connection is established. In step 206, data is uploaded to the web server and associated to a device ID and user. The web server responds in step 208 by sending messages to synchronize the data including a time and date stamp of last received data (clear log); a list of date and time stamps for reminders; and may include a down load list of device IDs associated with that hub.

FIG. 16 is a software flow diagram used to control the data server/portal in connection with user interaction. Initially, in step 210, data is received by the data server from the hub. In step 212, the data may be decrypted and staged for acceptance by the user after a user logs in. Subsequently, in step 214, the data is cataloged in a user data repository or database to enable the user to interact with the data in meaningful ways like display charts, tables and trigger alarms and trends. As indicated in step 216, the data may be checked against preset requirements for alerts and trends. These alerts and trends may be shown to the user in step 218 in various ways on a web page, a pager, a telephone, an e-mail to a selected list of people to be informed. The web server may then display the charts and tables in step 220. The reports and tables can be exported to spreadsheets and/or e-mailed to third parties in step 222 for review. In step 224, the server allows additional third party access for the various data in step 224.

As indicated in step 226, when connection, such as Internet connection, is established between the hub and the server, the server sends the hub various messages. These messages may include the current device ID list for the user to the hub. The messages may also include date and time stamps for reminders and the date/time stamp of the last updated reading.

Web Pages

Figure 17:
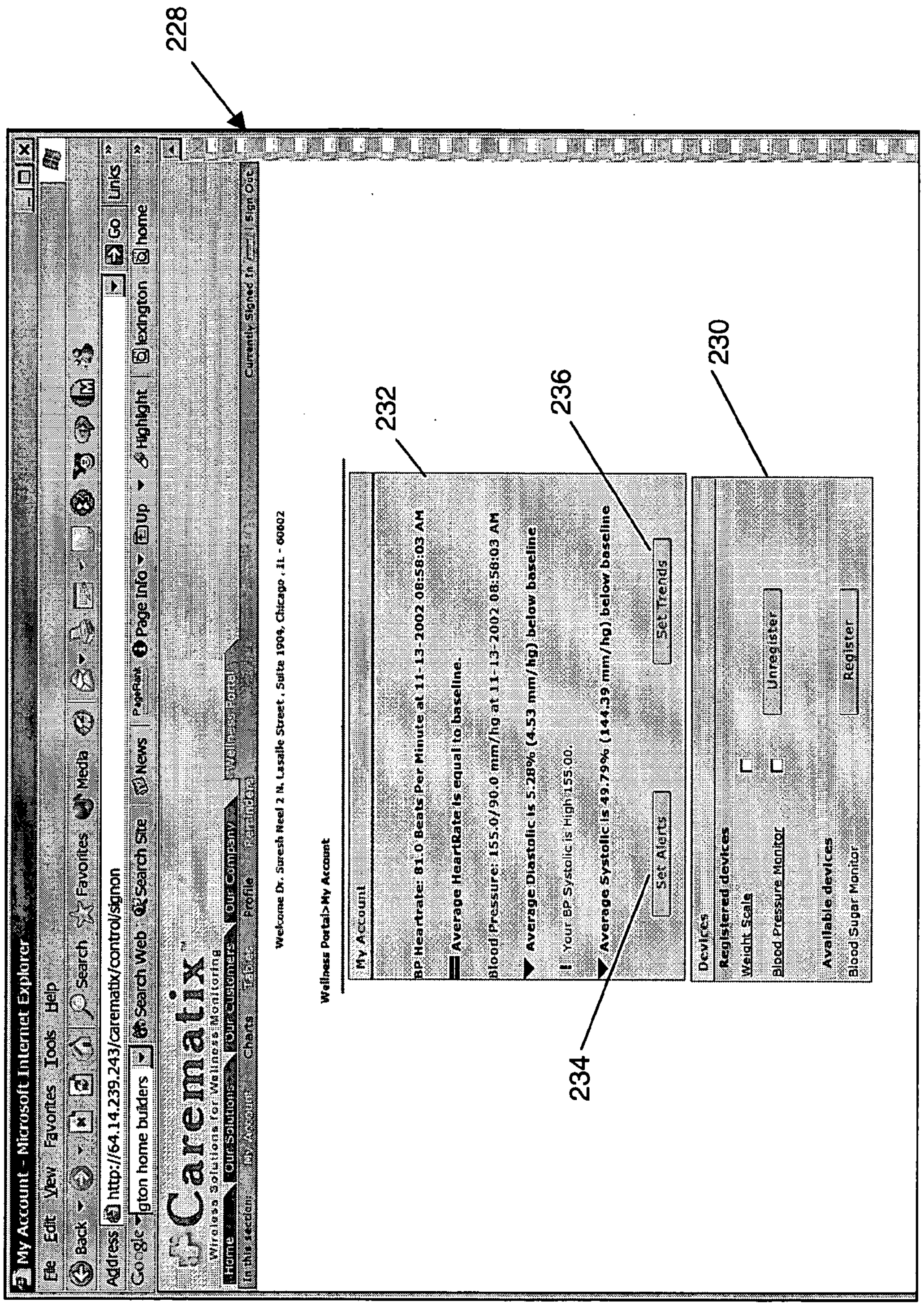
FIGS. 17-24 are exemplary screen shots for use with a web-based embodiment of the present invention.

In a exemplary embodiment, as discussed in detail below, the remote server may be configured as a web portal. Exemplary web pages for a patient monitoring system are illustrated in FIGS. 17-24. In particular, FIG. 17 illustrates exemplary home page generally identified with the reference numeral 228. This web page 228 includes a registration box 230 and an account box 232. The registration box 230 allows patients to register and unregister various physiological characteristic measurements. The account box 232 provides a summary of a patients' alert and trends. The account box 232 includes links 234 and 236 to screens where alerts and trends can be set.

Figure 18:
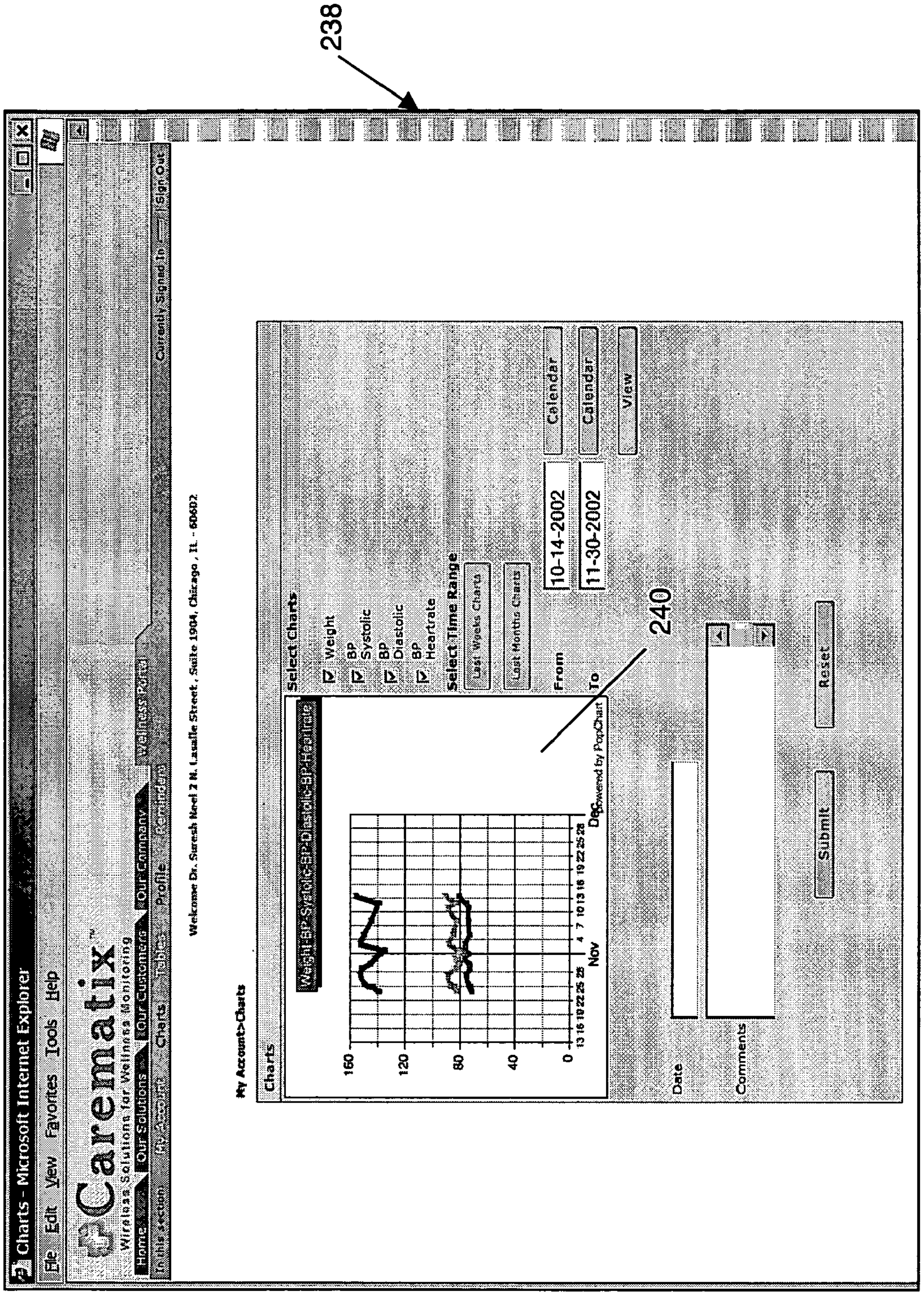
Figure 19:
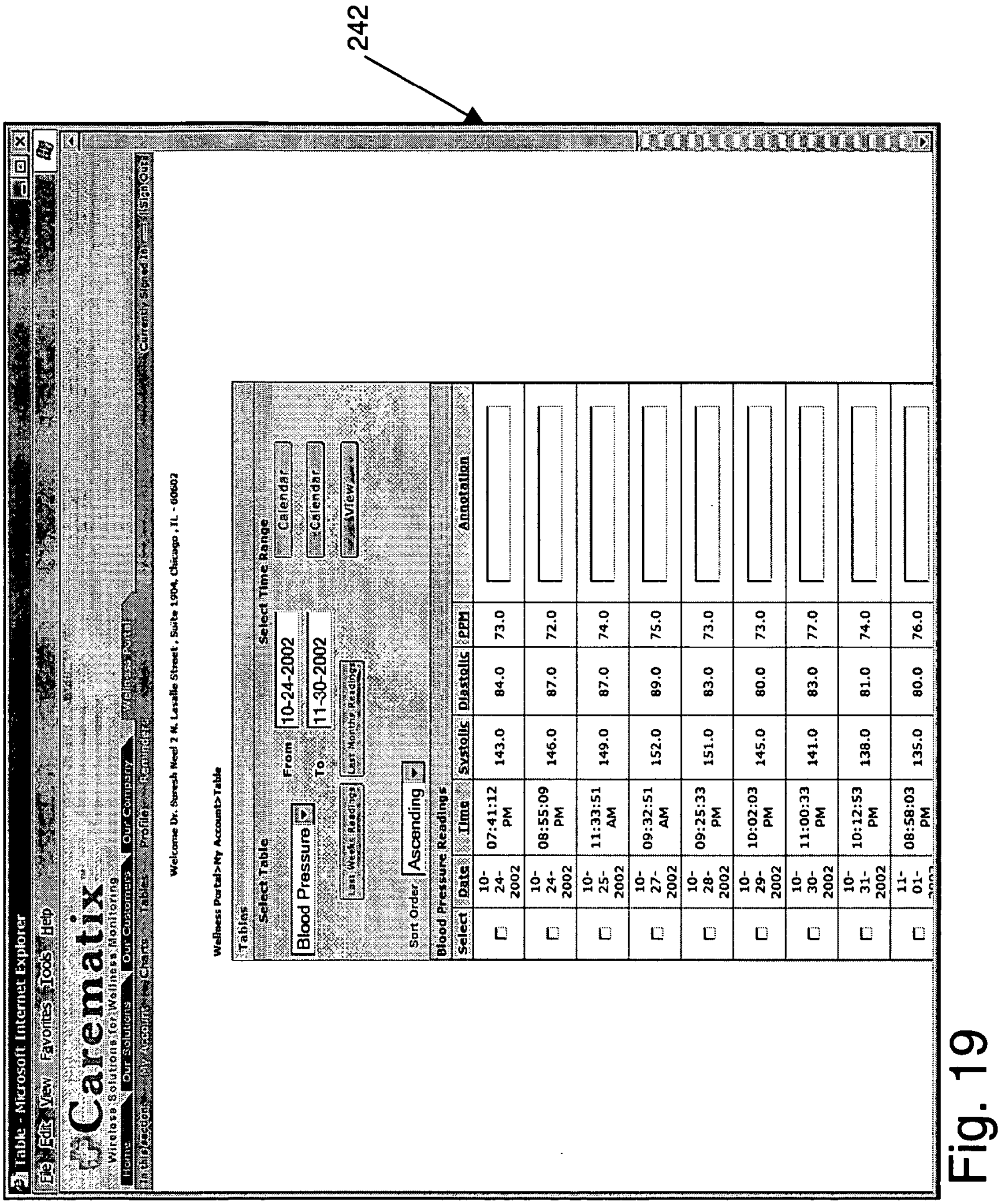
Figure 20:
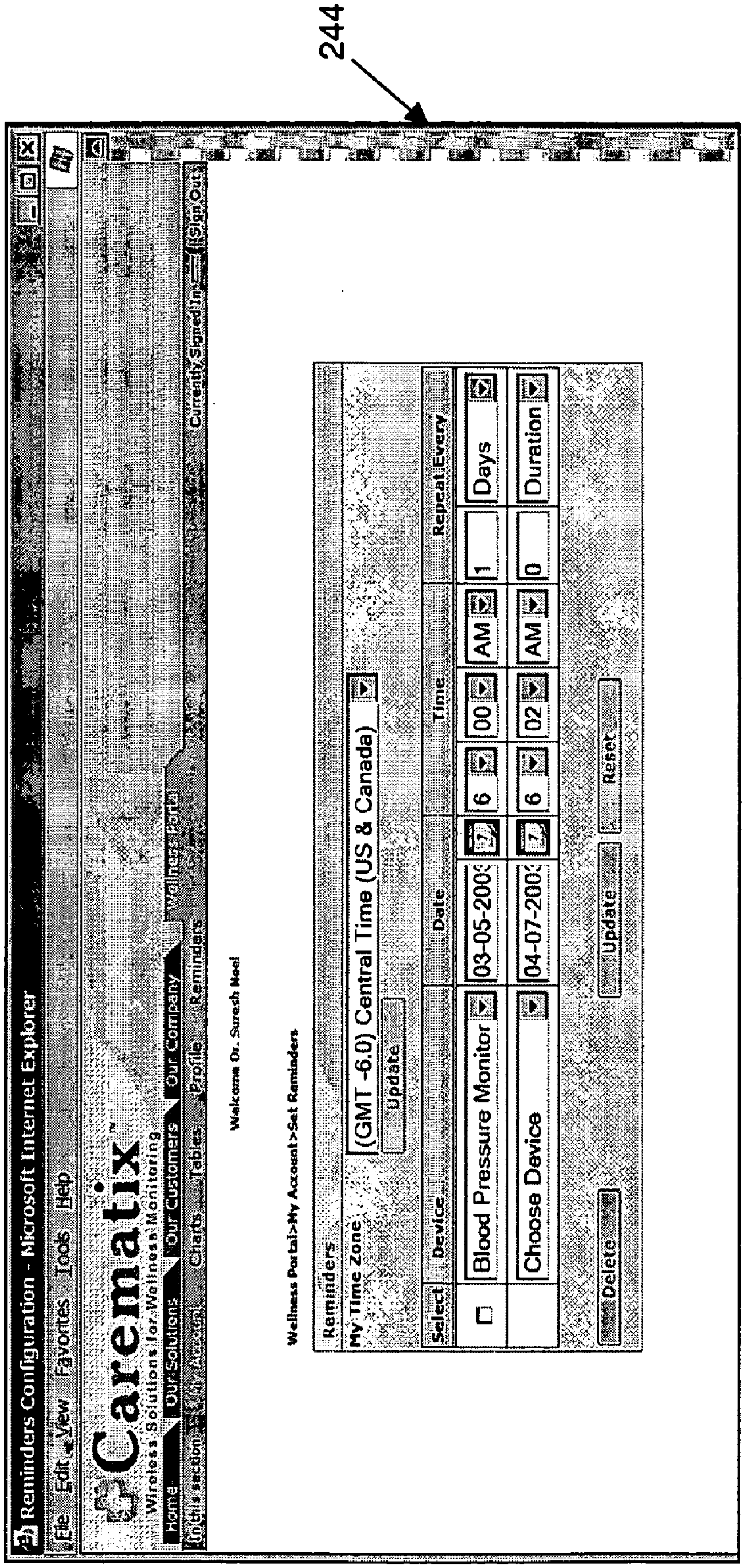
Figure 21:
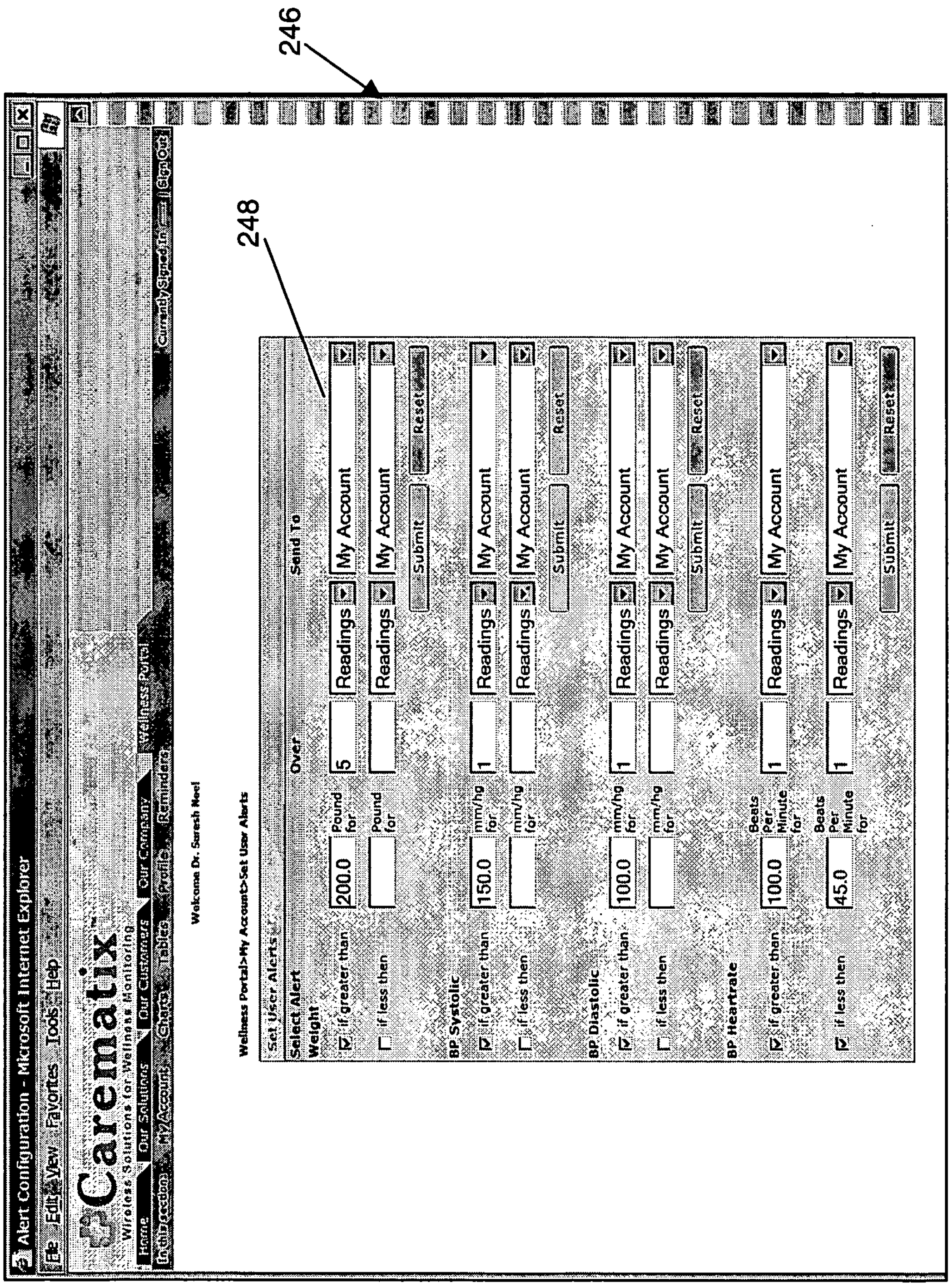
Figure 22:
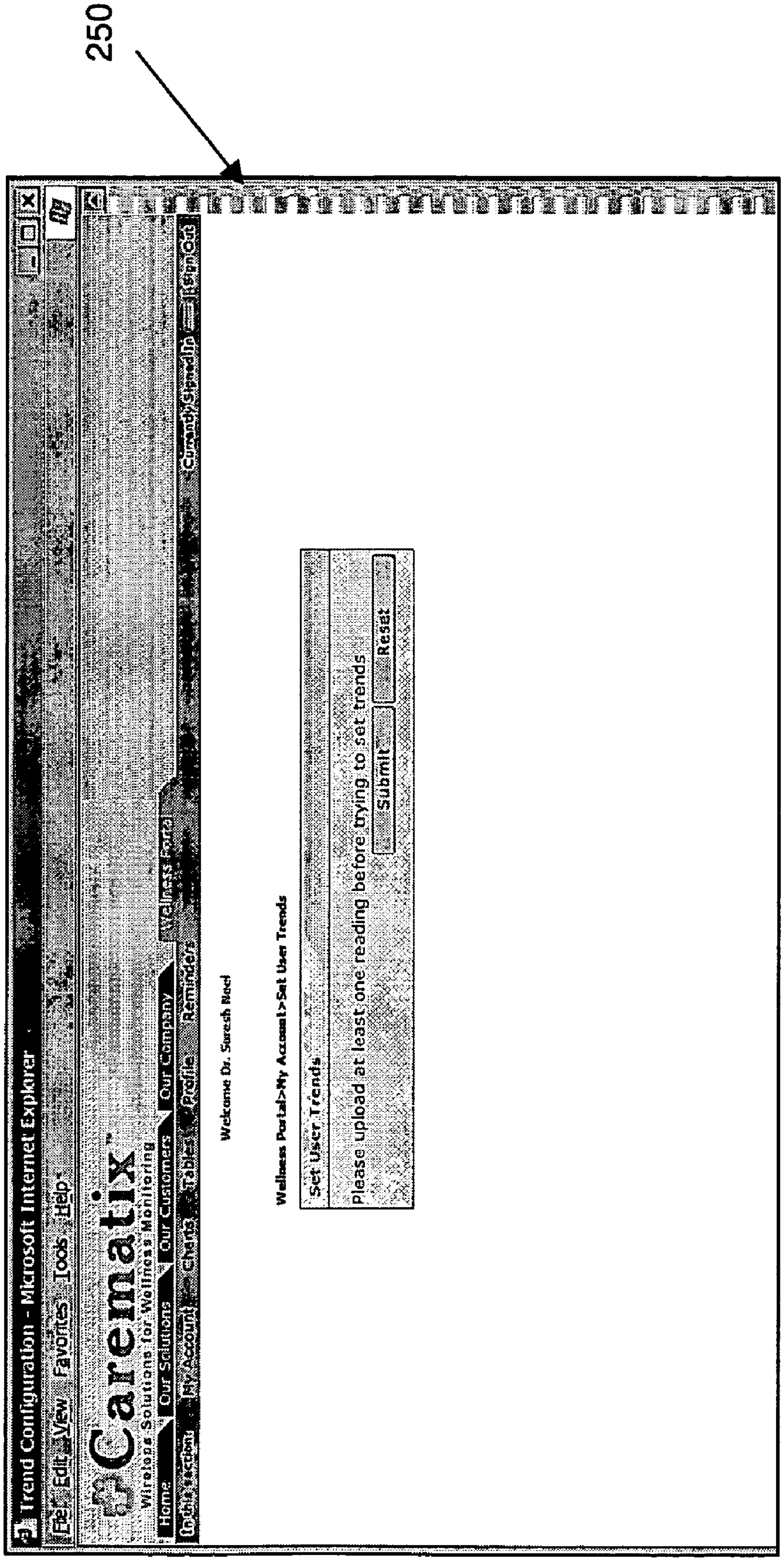
Figure 23:
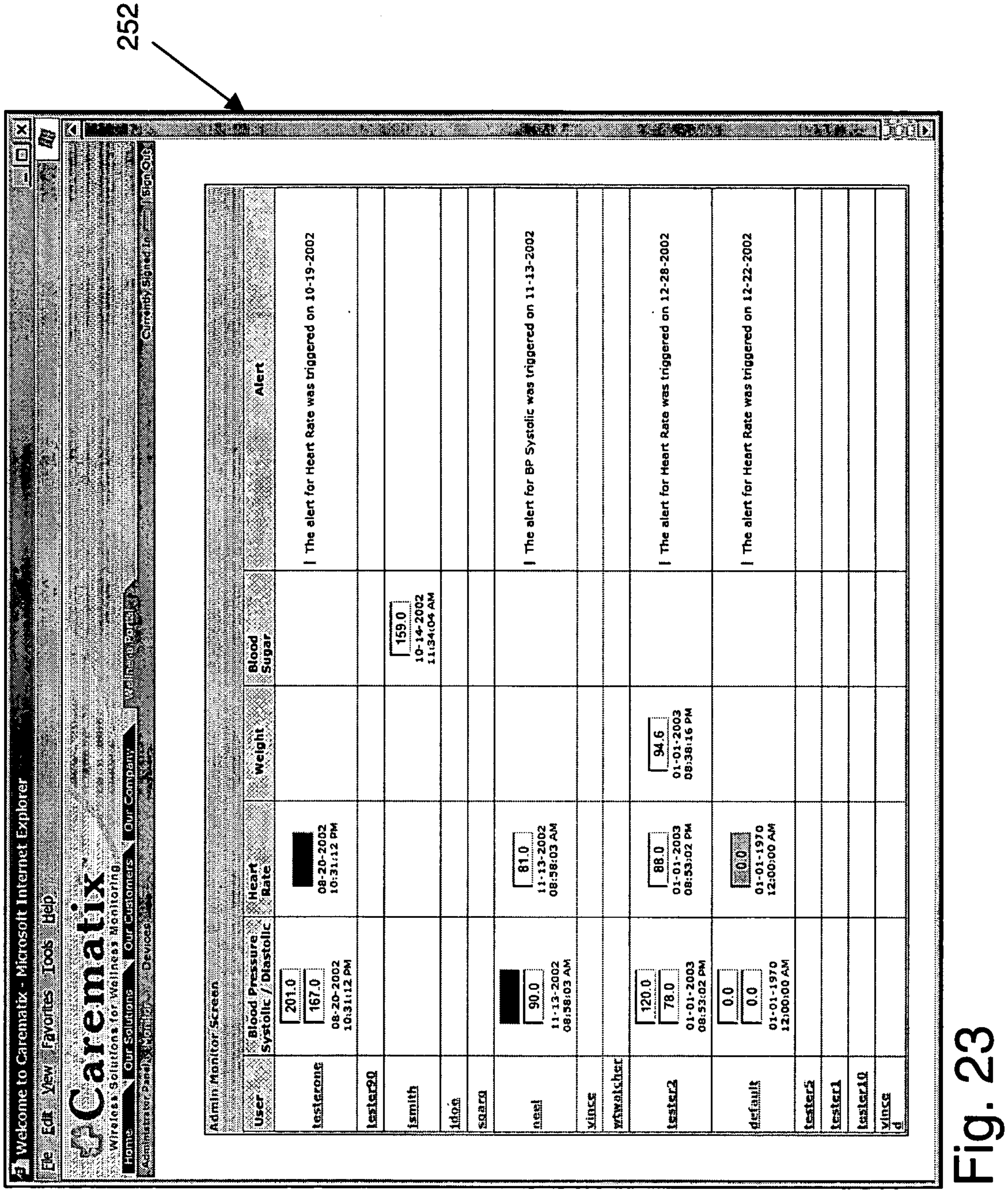
Figure 24:
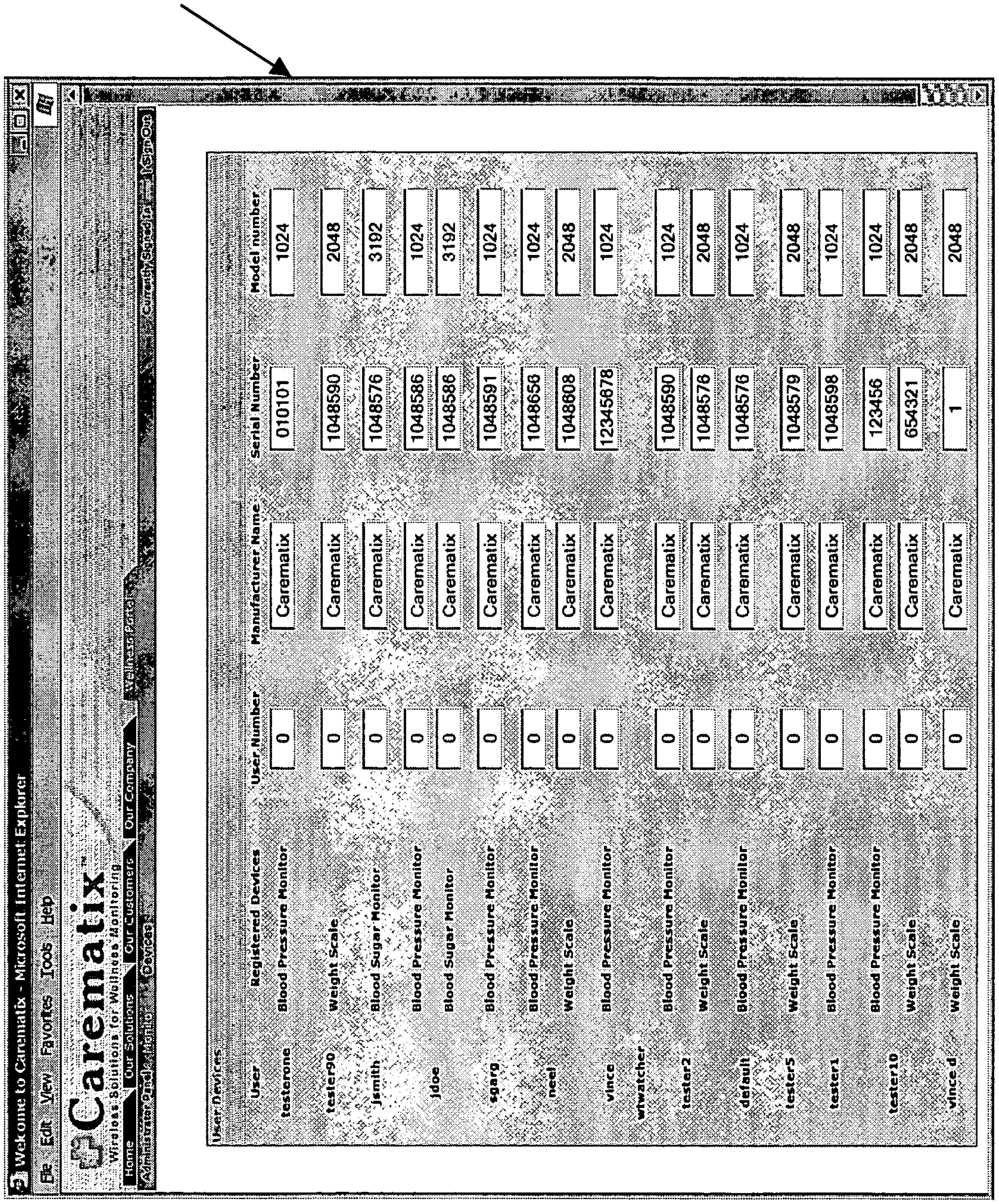

FIG. 18 illustrates a exemplary web page 238 which allows a user, either a patient or a third party user, to track data by way of a display window 240. The exemplary web page 238 allows a user to track data, view it by device type, change the time scale as well as annotate the data. FIG. 19 is an exemplary web page which allows a user to view data in tabular form. On this page, the time range and device data can be selected by the user. FIG. 20 is an exemplary web page 244 which enables a user to set reminders for the device to provide reminders, either aurally or visually at certain times or at periodic intervals. FIG. 21 is an exemplary web page 246 which allows a user to set alert parameters on absolute values and to specify how to receive the alerts via browser, e-mail, voicemail, pager, etc. In particular, "My Account" boxes generally identified with the reference numeral 248, allow the particular message link to be selected. FIG. 22 illustrates an exemplary web page 250. The web page 250 allows a user to set up parameters, baselines and trends. FIG. 23 illustrates an exemplary web page 252 which may be used by a clinical administrator to monitor a summary status of all assigned patients including the last reading and any alerts generated. FIG. 24 illustrates an exemplary web page 254 for use by an administrator to view the devices registered by various users in the system.

Server Application Architecture

FIG. 11 illustrates the server application architecture. The server application architecture may include four levels or tiers 228, 230, 232, 234. The tier 228 may be a user or client tier which allows users to interact with the underlying application. This client tier translates user actions and inputs them as server requests and formats a server response, usually visual. The client tier may be a client, such as a browser, or a custom application running on a hub or specific devices such as wired, wireless handheld Personal Digital Assistants (PDAs).

The client tier may also be a non-user action, such as automated services, such as Internet Explorer.

The web tier 230 makes application functionality available on the worldwide web. This tier 230 accesses data and business functionalities, manages screen flow and often encapsulates some user interaction. It may be used to decouple the client from the business logic tier 232 to provide a uniform service model of client request. The web tier interacts with other tiers using standard protocols. Other applications may take place of the client programs accessing the underlying application through its web tie, such as Apache/Tomcat.

The business logic tier 232 encapsulates the business logic and comprises the software application functionality. The logic is organized as a set of interacting objects allowing for additions and enhancement of the logic at any point while still preserving the interface of other tiers. This business logic tier 232 may be implemented using J2EE, Microsoft.NET or a custom architecture, such as Tomcat.

The data access tier 234 may be used to integrate the application with other enterprise information systems. This tier 234 provides data storage and other information services to the application. It may consist of a database, enterprise resource planning systems, mainframe transaction processors, legacy systems and enterprise integration technologies. Other tiers access these databases using industry standard or custom protocols such as Oracle.

Web Portal Details

As mentioned above, in one exemplary embodiment of the invention, a web portal (hereafter referred to as the portal) provides meaningful access to a patient's personal health data, as collected by the patient monitoring device(s) and stored in a server-based data repository (hereafter referred to as the repository). Some key mechanisms of the portal are listed below and are explained in further detail in subsequent sections. These key mechanisms include:

- A mechanism for self-registration of devices by the user.
- A mechanism to synchronize data between the Repository and device(s) via the Receiving Station.
- A mechanism to allow the user to preview the readings received from the device(s) and reject erroneous readings.
- A mechanism to generate alerts against received data, based on user defined parameters.
- A mechanism to determine trends in received data, based on user defined parameters.
- A mechanism to match computed trends with visual perception of the trend.
- A mechanism to set reminders on the device(s). This mechanism can be extended to set up any arbitrary "event" on the device(s) e.g. local alert generation.
- A mechanism by which a clinician may monitor a group or a number of users via a summary "dashboard" of their readings data, with ability to drill-down into details for each user.
- A mechanism to enhance user (healthcare) education by providing a healthcare questionnaire dynamically created (and updated) based upon certain rules applied to recent user readings data.
- A mechanism to provide data feeds (i.e. export, either "raw" or aggregated) to external systems with transformations between appropriate data formats.

Device Registration Through Portal

Device registration is the process by which a patient monitoring device is associated with one or more users of the system. This mechanism is also used when provisioning devices for a user by a third party, such as a clinician (or their respective delegate). The mechanism is as follows:

1. The user (or delegate) identifies himself/herself by logging into the portal. The user must have previously registered an account created either by themselves or by delegates.

2. User (or delegate) registers a device by:

a. Choosing from a list of kinds of devices available for registration.

b. Providing identification information for the device such as manufacturer information, device model information, device serial number (available on device packaging) and optionally a hub number (available on hub packaging). The user may register more than one device at this point.

c. Optionally setting up a service subscription for device(s) usage. This includes selecting service plans and providing payment information.

3. The device(s) are then associated with this user's account and a Device Control File (discussed below) comprised of device identification information is synchronized between the server and the Receiving Station on initialization (see the section Data Synchronization between Receiving Station and Repository). This enables the Receiving Station to respond to and accept input from the devices that have their identification information in the control file.

4. On each interaction between the hub and the server, the control file entries for the current user (or hub) are synchronized.

5. Similarly, whenever the user registers a device, its entry is added to the control file on the hub if not already there on the next synchronization interaction with the server.

6. No association information between the actual user (person) and the device is kept on the user's hub. This determination is made after the data is uploaded to the server.

7. The hub may be shared between users and data for all users resident on the hub is uploaded to the server on synchronization.

Device Control File

This file contains records in the format

<device id>, <data update timestamp> where <device id> is all the information required to uniquely identify a device to the system (such as manufacturer number, model number, serial number and user number) and the <data update timestamp> is the timestamp (including date) that data for this device was last received by the server. Note that this is not the timestamp for which data was last uploaded from this particular hub (on which the control file resides) but is the timestamp for which the server last received data (from any hub) for the particular (registered) device. Additional information for controlling the device(s) e.g. reminder information is also maintained in this file.

This file is internally maintained in XML format for ease of interfacing but is either kept encrypted or in a non-readable format on the hub for security reasons.

User Data File

This file contains records in the format

<device id>, <reading timestamp>, <reading data> where <device id> is as described in the section Device Control File. The <reading timestamp> is the time of the reading and the <reading data> is a data record in a format specific to the type of reading. This file is internally maintained in XML format for ease of interfacing but is kept encrypted or in a non-readable format on the hub for security reasons.

Data Synchronization between Receiving Station and Repository

The hub and the Repository frequently synchronize data. The hub may use one of various transportation methods to connect to the repository e.g. using a PC as conduit or via a connection established using an embedded modem (connected to a phone line) or via another network-connected device (such as, but not limited to, a web-phone, video-phone, embedded computer, PDA or handheld computer). The mechanism is as follows:

1. When a user logs into the portal, the User Data File, resident on the hub, is uploaded to server. The server filters duplicate readings records.

2. Alternatively, the Data Synchronization Client may upload the data from the hub to the Server without user intervention automatic data synchronization without user intervention also happens in the case of a stand-alone hub.

3. The data may be decrypted on the server, assigned to each user (by determining which user the device is registered with) and put into a staging area. This staging area is so that the user may optionally preview the data before accepting the values. The server also filters for duplicate reading values.

4. The device control file is uploaded to the server.

5. The server downloads updated device control file with last updated timestamps for each device in list. If device has been removed from the system, then its entry in the file is deleted. The old device list file is backed up.

6. The data file is cleared/deleted.

Data Synchronization Client

There is often the need for the reading data to be uploaded to the server without explicit user intervention. The Data Synchronization Client runs on the hub to upload the user's data to the server while synchronizing the information contained in the control file.

Alerts

Users may set up alerts that are triggered when one or more reading meet a certain set of conditions, depending on parameters defined by the user. The mechanism is as follows:

1. The user sets up an alert by choosing the condition that they would like to be alerted to and by providing the parameters (e.g. threshold value for the reading) for alert generation.

2. Each alert thus set up has an interval associated with it. This interval may be either the number of data points or a time duration in units such as hours, days, weeks or months, depending on the type of reading for which this alert is being set up.

3. The values of readings lying within the interval specified by the user must all either positively or negatively exceed the specified threshold for the alert to be generated i.e. there is an implied "and" across all the readings within the interval.

4. The user chooses the destination where the alert may be sent. This destination may include the user's portal, e-mail, pager, voice-mail or any combination of the above.

5. Specific, preset alerts are provided based on medically established conditions in the case of common reading types e.g. heart rate, weight, blood sugar etc. The user may modify the parameter values for these alerts if they so desire.

Trends

The system computes trends in the user's data values over an interval. The mechanism is as follows:

1. Trends are determined by applying mathematical and statistical rules (e.g. moving average and deviation) over a set of reading values. Each rule is configurable by parameters that are either automatically calculated or are set by the user.

2. Currently the system tracks deviations from baseline values (see section Baselines) either automatically calculated using intelligent defaults or provided by the user.

3. The user also supplies a range over which the trend is calculated. This is specified either as the number of data points or a numerical unit of time (e.g. hours, days, weeks etc, depending on reading type).

4. This range is always applied backwards from the most current reading i.e. if the user specifies that the trend needs to be calculated over the past 5 days, then the system will calculate the trend of the past 5 days from current date.

5. The system displays the deviation between the trend values computed from received data and the baseline value. This deviation is indicated both as a percentage as well as a numerical difference, along with icons ("+", "−", "=") to visually indicate the trend direction.

Baselines

6. The system may be used to calculate a baseline value for each reading type using algorithms specific to each reading type. The user can override the default baseline average by changing the default parameters used to calculate the baseline e.g. the start date and the number of readings. Additionally, the user may directly provide baseline value(s) into the system, overriding the computed baseline values. If the user provides parameters such that there is insufficient data for calculating the baseline, then the system alerts the use to the fact. Previously set baseline values are not altered.

During early use of the system, there may be insufficient data for automatically calculating baselines for the user's reading types. In this case too, the system alerts the user to the fact.

Strength of Trend Correlation

The system may contain algorithms to compute the strength of the trend and correlate it to the visual perception of the trend as would be observed by a human observer.

Example Algorithm: In order for a weight trend to be visually perceived as increasing or decreasing, a certain positive or negative standard deviation from a moving average baseline must be observed over a pre-defined time period to be able to inform the user that their weight is either increasing or decreasing.

```
old-baseline = calculate moving average for initial data range
old-standard-deviation = 0
for each subsequent interval
    new-baseline = calculate moving average for updated data range
    new-standard-deviation = standard-deviation(new-baseline, old-
baseline)
    if (new-standard-deviation > 0)
        then trend is increasing
        if standard-deviation(new-standard-deviation, old-standard-
deviation) > 0
            then strength of trend is increasing
        else strength of trend is decreasing
    else if (new-standard-deviation < 0)
        then trend is decreasing
        if standard-deviation(new-standard-deviation, old-standard-
deviation) > 0
            then strength of trend is increasing
        else strength of trend is decreasing
    old-baseline = new-baseline
    old-standard-deviation = new-standard-deviation
```

Reminders

The user may set up reminders on the device(s) via the portal. The device then draws the user's attention at the appointed time e.g. by sounding a buzzer. The mechanism is as follows:

1. Each device associated with the user's account has its own independent set of reminders.

2. Each reminder can be made repeatable. The user can set the reminder to repeat every n <units of time> (where <units of time> may be hours, days etc.) starting from a preset date and time.

3. The reminders are associated with a user's account and are synchronized with the device(s) via the hub. The reminder information is maintained in the control file (see section Device Control File).

4. The user can specify their time zone so as to account for differences between time on the server vs. the user's local time.

Buddy or Role Based Access

The user may give permission to others as needed to read or edit their personal data. This is useful, for example, for allowing a well-wisher to view ones data/charts, or receive alerts. The clinician could be allowed to edit data for example to annotate it, while the patient would have read-only privileges and that too for certain pages. An authorized person could set the reminders and alerts parameters with limited access to others.

The user or clinician could have a list of people that they want to monitor and have it show on their "My Account" page, which serves as the central monitoring station. The central monitoring concept could be particularly useful in an environment where on person wishes or needs to monitor multiple people.

Clinician Administrator

A clinician administrator (also referred to as Administrator in this context) may monitor the data for and otherwise administer a number of users of the system (also referred to as Patients in this context). The mechanism is as follows:

1. A summary "dashboard" of readings from all Patients assigned to the Administrator is displayed upon log in to the Portal by the Administrator. At a minimum, the Patient's last reading received from all devices is shown (color coded to visually distinguish normal vs. readings that have generated an alert), along with description of the alert generated.

2. The Administrator may drill down into the details for each Patient to further examine the readings data, view charts etc. in a manner similar to the Patient's own use of the system.

3. The Administrator may also view a summary of all the devices registered to all assigned Patients, including but not limited to all device identification information.

4. An Administrator has access only to information about Patients that have been assigned to the Administrator by a Super Administrator. This allows for segmenting the entire population of monitored Patients amongst multiple Administrators.

The Super Administrator may assign, remove and/or reassign Patients amongst a number of Administrators.

Patient Questionnaire

The Portal provides a mechanism to enhance the healthcare interaction and education of the users of the system (also referred to as Patients in this context). The mechanism is as follows:

1. A questionnaire may be made available to the Patient containing questions pertinent to their health condition.

2. The Patient's answers to the questions are stored and tracked by the time of each "session" (user interaction). Statistical summaries of these answers for various intervals of time are available for display.

3. The Administrator (or delegate) defines the entire set of questions that may be made available to all Patients. Of these, pertinent questions are selected based on rules applied to the Patient's recent data in the Repository.

Data Export and Reporting

Data may be extracted, exported and reported from the Repository into a variety of formats, both application specific and industry standard. The mechanism is as follows:

1. The data in the Repository is internally extracted into a neutral format represented in XML.

2. This data is further processed to either aggregate information or to remove user identification information, as may be the specific requirement.

3. The internal, neutral format may be transformed into custom, application specific formats or industry standard formats depending on specific application requirements.

Software Architecture Specification

Requirements

The architecture for the web application meets the requirements below. In particular, the architecture must be relatively independent of the user's client environment. At a minimum, the most common browsers (Netscape 4.0 and higher, IE 4.0 and higher) are supported on Windows (95, 98, NT, ME, 2000 now, XP in the near future). In addition, the architecture must be continuously adaptable to support newly emerging and evolving business requirements. This includes changes in the presentation, the business logic as well as the data tier.

In addition, the architecture should meet the following characteristics:

- Scalable to meet performance levels as the user base grows, with the cost of scaling contained for at least 300,000 users.
- Support rapid, iterative development. It is based on the J2EE Blueprints reference architecture with its timeline adapted to our schedule.
- Not require expensive development tools. Most of the development tools are available free as either open source or extended evaluation versions.
- Being based on industry-standard interfaces, it must allow for significant functionality to be purchased off-the-shelf (with integration and possible customization).

By adapting a standard reference architecture, it allows for the time required for developers to gain familiarity with the architecture to be compressed provided they are well versed in J2EE technology and architecture. This allows for the development effort to be outsourced at a later point in the development cycle. Moreover, the standard architecture, supports rapid and frequent changes to the look of the application. Such an architecture also supports the division of labor amongst the development team e.g. the application is partitioned such that the front-end designer requires minimal programming knowledge and vice versa.

The architecture should also partition the application to allow for the business logic to be accessed via a variety of interfaces e.g. the web (HTML) for now, wireless (WML) and/or voice response (VRU) in the future. It should also accommodate internationalization and localization of the application in the near future without significant changes. In addition, the architecture should leverage emerging technologies to provide a superior user experience e.g. it does not require the user to download, install and configure complicated software by utilizing emerging server-side technology. Moreover, the architecture should have a growth path to allow use of new technology as it becomes available over the application's lifespan (5 years). It should be designed to be resilient for at least the next 1-2 years while accommodating change. Finally, the architecture should not be tied to a particular set of products i.e. any J2EE compatible server can serve as application host. It also is relatively independent of database. This allows for flexibility in choosing and switching between hosting providers.

Technology

Platform

The Java 2 Enterprise Edition (J2EE) may be used as the standard technology platform for this application. Of the available J2EE components, the initial development phase may use Java Server Pages (JSPs), servlets, Java Database Connectivity (JDBC), Java API for XML Processing (JAXP). Other J2EE components, such as Enterprise Java Beans (EJBs), transactions APIs etc. may be used as required for subsequent development phases. Using J2EE components has the following advantages:

Simplified architecture and development

Scalability to meet demand variations

Integration with a variety of databases

Choices of servers, tools, components

Flexible security model

Relevant J2EE Features and Components

Scalability

J2EE provides mechanisms that support simplified scaling of distributed applications, without requiring significant effort on the part of the application development team. Because application services such as transaction support, database connections, life cycle management etc. are provided by the platform, the application can leverage these capabilities by adhering to the rules requiring it to be compatible with these services. For example, by using the appropriate JDBC APIs, connection pooling is automatically available for increased performance. Similarly, J2EE servers now provide many scaling mechanisms that were previously designed by the application developer.

Declarative Security

Security (access restriction, authentication) is configured declaratively at deployment time instead of being coded at development time. This allows for continuous refinement of the security mechanism (matching users with roles, with groups of users having specific access permissions) without requiring changes to the code followed by redeployment. For comparison, commercial products providing these kinds of capabilities for web applications (e.g. getAccess from Entrust Technologies) are typically priced at $15-$25 per user for quantities less than 5000 users.

Expandability

As the functionality provided by the J2EE expands, these capabilities are immediately available for use by the application. For example, the Connector architecture in the upcoming release of the J2EE will provide built-in capabilities of communicating with legacy systems (once commercial implementations are available).

Supported by Hosting Services

There are several commercial and open source implementations of J2EE compatible servers with the result that most hosting services offer reasonably priced hosting packages for J2EE applications.

Other Enabling Technologies and Products

Page Layout and Rendering

Flash

The pages should be as lightweight as possible while being aesthetically pleasing. This leads to using Flash as the rendering technology for items such as buttons and image maps etc. since this leads to compact graphics. However, there are no large animations.

CSS

The pages should not be hard-coded for a particular user screen size i.e. pages may be designed using Cascading Style Sheets (CSS).

Charting

Popchart (http://www.popchart.com) from Corda may be used to provide charting functions. It runs as an image server and services requests for charts from the web server over a pre-configured TCP port. It supports multiple output formats (including Flash, WML and SVG) and good chart interaction such as pop-up text and drill-down. The charts can be visually designed by a graphic designer and later rendered programmatically.

Reporting (Printing)

The reporting technology/product should support the following requirements:

It must be able to produce charts similar in nature to those produced on-screen for the user.

It must be able to export the user's data in Excel format for download.

It must be able to provide the user with the facility to print a report on his/her local printer.

It must be able to provide the user report in PDF format for use as an e-mail attachment.

The final choice of product is still pending. Among the products evaluated include Formula One from Tidestone Technologies and Style Report from Inetsoft Corp.

Development Tools

User Interface

Visual Design

Dreamweaver software may be used as a tool for developing the front-end HTML. Flash and (optionally) Fireworks software can be used along with Dreamweaver. MS Frontpage software, although popular, is not preferred since it introduces irrelevant HTML into each document.

Chart Design

Popchart software (see section Charting above) includes a graphics chart builder that allows charts to be interactively designed. The designer may use this builder to create aesthetically pleasing charts.

HTML Validation

All HTML should pass validation for acceptance. Tidy is one utility that can check HTML for validity.

Web Server

An Apache web server may be used for development. The deployment web server is provided by the hosting service.

Servlet Engine

Tomcat software may be used for development due to it providing integrated debugging with many IDEs (Integrated Development Environments) and its smaller memory footprint when compared with other similar commercial products.

Framework

J2EE Blueprints (JPS)

The current application architecture is modeled after the J2EE Blueprints reference application (the Java Pet Store version 1.1.1). Although EJBs are not used at this stage, the tier separation is maintained to allow them to be introduced at a later stage.

com.oreilly.servlet

This is a collection of utility classes available at www.servlets.com that may be useful in servlet development. Developed and maintained by Jason Hunter, author of the book Java Servlet Programming, 2nd Ed. (must read).

Java Code

Integrated Development Environment

Forte for Java, Community Edition may be used because it provides a rich feature set for free. JRun Studio has also been evaluated and may be used if we switch to JRun in a later development phase.

JSP Tag Libraries

Tag libraries from the Apache-Jakarta (and the Struts framework) project may be used if needed. Proprietary taglibs will not be used. Taglibs should be used if their use results in significant effort saving.

Code Documentation

Javadoc.

Build Tool

Any industry standard build tool (such as Ant or make) can be used as the build tool.

Unit Testing

The JUnit unit-testing framework (wwwjunit.org) may be used to unit test all developed code. Extensions to JUnit for server-side testing and J2EE testing (e.g. HttpUnit, Cactus) may also be used.

Database

Either Oracle or MS SQL Server 2000 may be used as the database. It is important to be careful to not have dependencies on the database to allow for switching if required by hosting providers.

Process Control

Configuration Management

Visual SourceSafe or CVS may be used. CVS is accessible over the Internet.

Bug Tracking

EbugStomp software may be used for web-based bug tracking.

Application Architecture

Request and Response Flow

This section describes the architecture of the application: exploring the partitioning of functionality into modules, the assignment of functionality to tiers, and object decomposition within the tiers.

Application Structure

Modules

This is a list of the functional modules of the system. Some of the modules are relatively simple but have been broken out to provide an idea of the broad functional areas of the application.

Control Module

This module provides the basic framework for the other functional modules. It provides key features such as navigation, security etc.

User Account Module

This module maintains information about a person's account (contact information, payment and credit card information) as well as the devices associated with a particular account.

User Profile Module

This module maintains information about a person's profile such as demographic information, medical conditions, medications and allergies.

Device Information Module

This module maintains information about the various types of devices supported by the system.

Data Synchronization Module

This module provides the functionality to upload the newly acquired readings data from a user's PC to the server. It flags potentially erroneous readings and provides a preview of the data so that the user may optionally reject some readings. Please refer to the section Data Synchronization between User's PC and Server for more details.

Data Management Module

This module manages the data obtained for each user. It also provides functionality to associate annotations with data points.

Data View: Charts Module

This module provides the functionality for the user to view his/her readings data as charts. The user may choose to view either preset ranges of data or choose an arbitrary range.

Data View: Tables Module

This module provides the user with a tabular view of their data. There are no complex table-editing functions.

Trends Module

This module contains the logic to provide the user indication of certain trends in their data.

Alerts Module

This module provides the functionality where the user can select from preset patterns to look for in the data to be alerted about. The user may choose certain parameters of the triggering events e.g. if their blood pressure is above X for Y days, then trigger an alert, where X and Y are chosen by the user.

Reminders Module

The reminders module generates preset reminders to a user about certain events that were supposed to have occurred but have not.

Groups Module

This module will provide functionality in which the user can choose to invite another registered user to be a part of his/her group. The invited user can then have access to the inviting user's data.

E-Mail Module

This module provides the functionality to send e-mail arising from a number of places in the application: when an alert is generated, for sending a user report etc.

Report Module

The report module will provide functionality to generate simple reports for the user incorporating charts.

Print Module

This module will provide the functionality to print on the client PC.

Export Module

This module provides the capability to export the user's data in Excel format.

Interfaces

The web application will have the following interfaces with external systems. These interfaces may be either synchronous (i.e. online, in real time) or asynchronous (i.e. as a batch operation, deferred in time).

Interface with Credit Card System

The application will transmit the user's credit card number and obtain online verification. It will also make periodic charges to the credit card as the user's account is automatically renewed on expiry.

Interface with E-Store

An outsourced e-store will provide the capability for a user to buy a device online. The application should be able to transfer information such as credit card information etc. to this system. Additionally, the front-end for such a system needs to be created and integrated with the rest of the application.

Interface with Refund Generation System

This system will generate pro-rated refund checks for users canceling their accounts. The application must transfer the required information to this system.

Interface with Customer Support System

A customer support system providing (at least) e-mail based support needs to be integrated with the application/site.

Interface with Device Control Software on the User's PC

At this time, the interface with the device control software running on the user's PC is asynchronous and is handled by uploading and downloading files to a known location on the user's disk. This will eventually be enhanced to obtain the file location from the Windows registry.

Key Mechanisms

Business Object Framework

The Business Object Framework (BOF) is designed as a lightweight stand-in for Enterprise Java Beans (EJBs). The idea is to create structural parallels with the EJB component structure (such as the home and remote interfaces, session and entity beans etc.) in a simple object framework that allows for easy migration to EJBs at a later time. The key differences between EJBs and BOs are:

There is no container that the BOF objects (and their derived objects/components) run in. Because of that, BOF-derived objects must manage their own lifecycle such as creation and destruction. This is however minimal and is abstracted behind utility (factory) methods.

BOF-derived objects are generically referred to as BOs (for business objects) and are packaged in the bo package within the application structure. The scope of BOs is the same as for regular Java objects. This is different from EJBs, whose scope is controlled by the container and managed by methods on the home interface. The BO implementation objects must directly implement the BOF equivalent of the remote and home interfaces i.e. the BOInterface and BOHome. This is a key distinction from EJBs, in which the implementation object does not directly implement its home and remote interfaces.

The methods in the BOHome that are implemented by the BO have the same names as defined in the interfaces. This is different from EJBs which have a naming convention of prefixing ejb to the method name e.g. ejbCreate for a method named create in the home interface. BOs extend either the SessionBO or EntityBO base class. This is different from EJBs, which instead implement either the SessionBean or EntityBean interfaces. BOs are not remotely referenced and execute in the local JVM instead.

Components

The BOF has the following main types of components as set forth below:

Business Object Interface

This is the equivalent to the EJB remote interface. All business process methods are defined in this interface. Interfaces of this type extend com.carematix.bof.BOInterface and are named per the EJB convention i.e. using the domain class name. The BO must implement this interface directly.

Business Object Home (Interface)

This interface is the equivalent of the EJB home interface. At the very least, it must define a create( . . . ) method to return a concrete BO object implementing the BOInterface. Interfaces of this type extend com.carematix.bof.BOHome and are named per the EJB convention i.e. by appending "Home" to the domain class name. The BO must implement this interface directly.

Business Object

This is the abstract base class (com.carematix.bof.bo) for Session Business Objects (SBOs) and Entity Business Objects (EBOs) described below.

Session Business Object (SBO)

An SBO is the equivalent of a session EJB. One key distinction is that SBOs can only be stateless, not stateful beyond the scope of the calling method. It is best to assume them as stateless. Typically, SBOs define most of their methods in the BOInterface and have just a simple create( ) method in the BOHome interface. A session BO extends the base class com.carematix.bof.SessionBO.

Entity Business Object (EBO)

An EBO is the equivalent of an entity EJB and encapsulates some persistent data representation. Typically, EBOs have a simple BOInterface and have most of their methods in the BOHome interface such as create( . . . ), load( . . . ), store( . . . ), remove( . . . ), findByPrimaryKey( . . . ) etc. Not all of these methods are required in every EBO and only those needed by the application must be defined. An entity BO extends the base class com.carematix.bof.EntityBO.

EXAMPLES

Source code for the placeholder classes comprising the BOF is available. Accompanying that are two example packages: boexample1 and boexample2. These provide example implementations for a session BO and entity BO respectively. They illustrate the patterns and conventions required to create BOs and should be thoroughly studied.

Usage

In order to access a BO from calling code, the following example of a handler method for handling account events is illustrative:

public void perform(PWMAppEvent event) throws PWMAppEventException

```
{
  AccountEvent ae = (AccountEvent)event;
  ...
  switch (ae.getActionType( ))
    {
      case AccountEvent.CREATE__ACCOUNT:
      {
          try
          {
            UserHome userHome = BOUtil.getUserHome( );
            User user = userHome.create( );
            user.createAccount(ae.getUserId( ), ...);
            ...
          }
          catch (DuplicateKeyException dke)
          {
            ...
          }
          // Catch more exceptions
        }
    }
}
```

Deployment

Entries need to be created in the web.xml file for each BO in order to enable JNDI lookup. Entries for the BO examples are as follows:

```
<?xml version="1.0" encoding="ISO-8859-1"?>
<!DOCTYPE web-app PUBLIC '-//Sun Microsystems, Inc.//DTD Web Application 2.2//EN' 'http://java.sun.com/j2ee/dtds/web-app__2.2.dtd'>
<web-app>
. . .
<env-entry>
<env-entry-name>bo/boexample1/Example1</env-entry-name>
<env-entry-type>java.lang.String</env-entry-type><env-entry-value>com.carematix.boexample1.bo.Example1SBO</env-entry-value>
</env-entry>
<env-entry>
<env-entry-name>bo/boexample2/Example2</env-entry-name>
<env-entry-type>java.lang.String</env-entry-type><env-entry-value>com.carematix.boexample2.bo.Example2EBO</env-entry-value>
</env-entry>
<env-entry><env-entry-name>bo/boexample2/Example2DAOClass</env-entry-name>
<env-entry-type>java.lang.String</env-entry-type>
<env-entry-value>com.carematix.boexample2.dao.Example2DAOImpl</env-entry-value>
</env-entry>
. . .
</web-app>
```

Template Mechanism

The XML-based templating solution provides many benefits. XML is a useful, consistent way of representing application parameters. The XML format is easy to use for both presentation specialists and third-party tools. The fact that XML is standardized means we can use off-the-shelf software to handle all the details of parsing and writing our screen definitions, configuration files, and other forms of structured data. Finally, XML can be validated against a DTD (Document Type Definition), so the parser can handle errors relating to ill-formed input, instead of in the application code.

Three files control the templating system:

The template file (template.jsp), which defines the basic layout of all of the pages generated from the template. There is one template file per supported language.

The request mappings file (requestmappings.xml), which maps virtual URLs to screen names (or request handler classes). There is one request mappings file in the application.

The screen definitions file (screendefinitions.xml), which defines the parameters for each screen. There is one screen definitions file per supported language.

The main controller servlet MainServlet receives incoming HTTP requests. MainServlet matches the incoming url to the URLs defined in the request mappings file, obtaining a screen name. The template parameters corresponding to the screen name are retrieved from the screen definitions file, and the template is then served using those parameters. The MainServlet does not do all of the work. Most of the work is delegated to other classes that specialize in screen flow management, template instantiation, and the like.

The XML files in the templating system are parsed by a standard XML parser, created using the JAXP (Java API for XML Parsers) optional package. The template is served as a JSP page, and the inclusion of the dynamic content occurs because the JSP engine calls the custom tag <j2ee:insert> each time it occurs.

In a Web application, each screen presented to the user can be considered as a different view. However, unlike the classic MVC architecture, all these views share the same controller. There needs to be a mechanism that allows the controller to choose a particular view to render in response to a user request. In the sample application, the controller makes this selection by specifying the screen ID of the screen to present as the response. This screen ID is mapped to a screen definition, then the template is instantiated. Recall that the file template.jsp defines the template for the sample application. This file includes another file, ScreenDefinitions.jsp, which defines all the screens of the sample application. When the controller invokes the template file at request time, it sets the appropriate screen definition in the request scope. The template file passes this information to the screen definitions file which then returns the appropriate screen definition for the request. One goal in structuring template and screen definition files is to facilitate internationalization (discussed in Section 4.5). This is achieved by separating text content from Java code. Since screen definitions that contain direct and indirect parameters are candidates for internationalization, we want to keep ScreenDefinitions.jsp devoid of Java technology code. We achieve this through the use of JSP custom tags.

Data Access Mechanism

The application uses a bimodal data access mechanism to increase efficiency of data access. Since it is anticipated that the majority of data access will be read-only (50% or more, as a conservative estimate), the data access mechanism will not utilize a transactional component for reading, relying instead on direct JDBC access to reduce overhead. Conversely, data updates will still continue to rely on a transaction component. When a transactional update does occur, the model will be refreshed from the data store and a model update event propagated to all registered views to update themselves, ensuring data display consistency.

Data Synchronization Between User's PC and Server

The functional specifications for the data synchronization mechanism are listed below, followed by details on each of the components that implement the mechanism. In cases where the implementation details of a component is not yet decided (such as whether to use an applet or not on the client PC), it is referred to generically (e.g. data sync client).

Functional Specifications

When a user logs on to the home page (FIG. 17) using the PC the data file is uploaded to server. The server filters duplicate readings records. The records are decrypted on the server, assigned to each user (by determining which user the device is registered with) and put into a staging area. This staging area is so that the user may optionally preview the data before accepting the values. The device control file is uploaded to the server. The server downloads updated device control file with last updated timestamps for each device in list. If device has been removed from the system, then its entry in the file is deleted. The old device list file is backed up. The data file is cleared/deleted. If a user has logged onto the site for the first time from this PC, then a new control file is downloaded. This control file will contain entries for the registered devices of the current user only and will be built up as other users log into the PC. Similarly, when a user registers a device, its entry is added to the control file on the PC if not already there.

For this phase of implementation, the locations of the control file and the data file on the user's PC is fixed. Note the following:

No association information between the user and the device is kept on the user's PC. This determination is made after the data is uploaded to the server by matching the device id against the RegisteredDevice table.

Data for all users (i.e. from all devices in the control file) is uploaded to the server, regardless of the user logged on.

Device Control File

This file contains records in the format

<device id>, <data update timestamp> where <device id> is all the information required to uniquely identify a device to the system (such as manufacturer number, model number, serial number and user number) and the <data update timestamp> is the timestamp (including date) that data for this device was last received by the server. Note that this is not the timestamp for which data was last uploaded from this particular PC (on which the control file resides) but is the timestamp for which the server last received data (from any user PC) for the particular (registered) device.

User Data File

This file contains records in the format

<device id>, <reading timestamp>, <reading data> where <device id> is as described in the section Device Control File. The <reading timestamp> is the time of the reading and the <reading data> is a data record in a format specific to the type of reading. Each record in the file is individually encrypted (encryption to be implemented in a subsequent phase) and is appended to the end of the file. Note that data for all users is aggregated in the same file.

Data Synchronization Client

This client runs on the user's PC to handle the file operations to and from the server such as uploading and downloading, checking for file existence, creating backup files etc. Note that these are all file operations and do not require any business logic in this client. All of the business logic decisions are made at the server and the appropriate files are downloaded. This allows for the client to be implemented as a signed applet.

A standalone Data Synchronization Client that does not require a PC and is directly able to connect to the server via a network connection is developed by embedding the synchronization logic in the firmware of a microcontroller and using it to connect to the server through a connection established either via a phone line (which requires an embedded modem) or via a connection established by another network terminal such as a web-phone or video-phone to which the Data Synchronization Client is connected.

Data Synchronization Manager

The Data Synchronization Manager component runs on the server and is the primary interface between the Data Synchronization Client and the rest of the application. Its primary operations include: receiving upload of the data file from Data Synchronization Client; decrypting the data records; determining which user each record belongs to (from RegisteredDevice mapping); putting each user's respective records in staging area (table) for user preview if so specified. This function is actually delegated to the ReadingsManager; putting each user's respective records in data tables if user does not want preview. This function is actually delegated to the ReadingsManager; signaling Data Synchronization Client to delete data file; receiving upload of control file; if control file does not exist, then creating it initially; updating control file with last uploaded timestamp for each registered device; downloading updated control file to Data Synchronization Client.

The Data Synchronization Manager has the following invocation points:

On user login.

On user registering one or more device(s).

On user previewing uploaded data prior to accepting it.

On an embedded Data Synchronization Client connecting to the server.

The Data Synchronization Manager is implemented as a Session BO as well as a standalone server application known as the iModem server.

IModem Server and Protocol Specification

The key attributes and mechanisms of the iModem server (i.e. Data Synchronization Manager for Standalone Data Synchronization Clients) are:

Accept multiple connections over the same server port at the same time: This will happen (in production) since more than one iModem could be connecting to the server and will require that the server be multi-threaded, using an independent thread for handling each connection. This is somewhat analogous to how web servers handle HTTP, which is a stateless protocol wherein several clients connect over the same port (80) at the same time. This also implies that the port number to which the iModem connects will remain constant.

Build in a versioning scheme into the protocol: This allows for upgrades over time without breaking backward compatibility.

Provide a status value in each message response. Zero indicates OK, non-zero values indicate various error conditions.

Error handling: There must be enough error handling and recoverability that a user's data is never lost and that each end (iModem or server) can signal to the other that data transfer either occurred or not. There must also be timeouts to handle conditions when no response is achieved. The value of the timeout (in seconds) must be a parameter read from a configuration XML file.

Break down current messages into multi-step messages: This is to handle two basic limitations: 1) each message to and from the iModem must be less than 256 bytes and 2) the iModem embedded code is more efficient in parsing fixed-length responses rather than variable length responses.

Encryption and keys: A basic mechanism (using placeholders as necessary) needs to be put in place such that in case the data stream is intercepted by a third party, all information that is private to the patient (such as reading values) and all information that can be correlated to deduce the message format (such as device identification information) is scrambled or encrypted.

This servlet is a "listener" for an embedded internet-modem (iModem) that has established a dial-up connection with a PPP server and is then communicating over TCP/IP to a specific server and port. The primary purpose of this servlet is to accept TCP connections over the specified port, parse the data coming over the connection and return responses. It also does basic connection management of connections and sockets as necessary. The incoming data stream comprises a series of messages in a simple protocol detailed below. This servlet parses the data stream, decodes the protocol message and responds based on logic detailed below. In summary, this servlet serves as a protocol handler for the iModem hub data transmission, which is done over TCP/IP sockets.

IModem Protocol.

The data protocol is a variant of the data exchange (XML) protocol that is used by the main web application for data interchange (defined by the files devicecontrol.xml and readingsdata.xml, hereafter referred to as the Datasync protocol). It differs from the Datasync protocol in the following manner to allow for the limited processing requirements of the iModem hub:

Numeric values are specified as hexadecimal text with each byte value comprised of 2 ASCII characters i.e. a decimal value 1085, which is 43D hex (or 043D hex, more accurately), will be specified as the characters '0', '4', '3'and 'D'. The most significant byte (MSB) is first when decoding multi-byte values.

Descriptive tags in the Datasync protocol are replaced with 4-digit hexadecimal numbers referred to as tokens. E.g. a <control-entry> tag may be denoted as <04AD>[1]. The mapping of the tags in the Datasync protocol to the iModem protocol must be configurable via another XML file (tagmappings.xml) so that it may be changed as the protocols evolve. End tags are denoted by a 4-digit hex number that is calculated by setting the most-significant-bit (MSB) of the number denoting the start tag. This defines the start tag and end tag relationship of the iModem protocol.

[1]The angle braces <>will still be used to surround tags

Readings are sent serially as a series of Readings Data messages (see below). This is given the current limitation of the iModem restricting the message length to be less than 256 bytes. The server response is either a success or error indicator.

All timestamps are in seconds elapsed since Jan. 1, 1970, denoted as a 4-byte number and encoded as the ASCII representation of the hex digits, MSB first. There is an additional command for getting the current server time that is not part of the Datasync protocol. The details of this message are defined below, with a descriptive tag being used in place of a token for illustration purposes.

Initiate Session

Command

<initiate-session><hub-id>H3H2H1H0</hub-id><protocol-version>P1P0</protocol-version></initate-session>

Response

<initiate-session><status>S1S0</status><current-time>T3T2T1T0</current-time><update-flag>F0</updateflag><key>K1K0</key><initate-session>

Details

The HubID is an identifier that is encoded in the iModem hub and is transmitted as a means of identifying itself. It is a long i.e. 4 byte number. This ID will be populated in the database through the device registration UI (which will be enhanced to support this later) and is used to associate a user (and his registered devices) with a specific hub.

On receiving this message, the server should set up a "session" with this connection and Hub ID and return a status code of 0000 in the response. All subsequent messages coming over this connection are considered in the context of the established session. If an unrecognized Hub ID is received, a status code of 0001 is returned with other message data being same. The <protocol-version> value is two byes, with the MSB being the major version and the LSB being the minor version. So currently, this value would be 0101 (current version is 1.1=>1<<8+1=257 decimal=0101 hex, formatted as 2 characters for each byte).

The response returned is the current server time, in seconds elapsed since Jan. 1, 1970. It is a 4-byte number and is encoded as the ASCII representation of the hex digits, MSB first.

There are two additional fields added for version 1.1. These are the update-flag and key. <update-flag> is a byte value that is used to signal to the iModem that there are parameter updates (see message Parameter Updates) that it needs to query for. The intent is to provide a way for parameters such as dial out numbers, dialing prefixes etc. to be provisioned via a web interface and indicated to the iModem so that it can update its own memory-based parameters. For version 1.1, the value returned is always 00 (zero).

The <key> is a placeholder value for now. It is a 16 bit number and its value is always 0000 (zero).

Parameter Updates

Command

<param-updates></param-updates>

Response

<param-updates><status>S1S0</status></param-updates>

Details

This is a placeholder message for now and will be expanded in future protocol revisions. The status code is always 0000.

Readings Data

Command

<readings-data><reading-record><device-id><manufacturer-no>M2M1M0</manufacturer-no><device-model>D2D1D0</device-model><serial-no>N3N2N1N0</serial-no><user-no>U0</user-no></device-id><timestamp>T3T2T1T0</timestamp><reading><reading-type>BP-HR</reading-type><units>mm Hg</units><values><bp-systolic>V0</bp-systolic><bp-diastolic>V0</bp-diastolic><pulse-rate>V0</pulse-rate></values></reading></reading-record></readings-data>

Response

<readings-data><status>S1S0</status></readings-data>

Details

This message is a fixed-format equivalent to the readings-data.xml file containing a single reading. The appropriate token values (as set up in tagmappings.xml file) are used for <reading-type> and <units> tag values.

The <status> value is a 16-bit integer. The value 0000 (zero) indicates no error whereas non-zero values indicate error conditions. Currently, only the value 0001 is assigned as a general error indicator. This list of values will be expanded over time and the code should be written to allow for it without significant change.

Because the iModem requires a fixed-length, fixed-format data command, the server must do some conversion/transformation to derive the application-specific XML <readings-data> command. The iModem will always send all data (BP, weight or blood sugar) in the format described above (for BP). The only difference for weight and blood sugar will be that the <reading-type> and <units> will correspond to the type of reading, so that for weight, <reading-type> value is WEIGHT and <units> value is POUNDS and for blood sugar, <reading-type> is BLOODSUGAR and <units> value is mg/dL. The value of the reading is derived from the byte values contained in the <bp-systolic>, <bp-diastolic> and <pulse-rate> tags. Because of this, the <value> tag is no longer required.

The server must use the following algorithm/logic to convert these fixed format iModem <readings-data> commands to the Datasync protocol's <readings-data> messages:

```
if (reading-type == BP-HR)
    then translate iModem <readings-data> message directly into
Datasync <readings-data> message
else if (reading-type == WEIGHT)
    then
        value = ((<bp-diastolic> << 8 + <bp-systolic>) >> 6) * 2.2
        // this value is in POUNDS, << & >> are left-shift & right-
shift operations
else if (reading-type == BLOODSUGAR)
    then
        value = <bp-systolic>
```

Number of Devices

Command

<device-control-list></device-control-list>

Response

<device-control-list><status>S1S0</status><num-devices>N0</num-devices></device-control-list>

Details

This command is used to obtain the number of devices currently registered by the user. The status is generally expected to be 0000, non-zero indicates an unspecified (as of yet) error.

Device Information

Command

<device-info><device-num>N0</device-num></device-info>

Response

<device-info><status>S1S0</status><control-entry><device-id><manufacturer-no>M2M1M0</manufacturer-no><device-model>D2D1D0</device-model><serial-no>N3N2N1N0</serial-no><user-no>U0</user-no></device-id><reminders></reminders><first-association-timestamp>T3T2T1T0</first-association-timestamp><last-update-timestamp>T3T2T1T0</last-update-timestamp></control-entry></device-info>

Details

The iModem sequentially requests device details for each device registered by the user, passing in a device number (actually, device index) as part of the command. The list is zero-indexed i.e. the first device is 0 (zero) and the index increments sequentially from there. The information in the response is the same as a single-entry device control file. Currently, nothing is returned for reminders (even if there are some set) since the iModem is not set up to handle them. These will be handled in a subsequent protocol revision.

Terminate Session

Command

<terminate-session></terminate-session>

Response

This command does not return a response.

Details

This command is for the iModem to indicate to the server that it is done with the session prior to terminating the connection so that the server may release resources and perform other cleanup. The server does not return a response to this command since the client's state is undefined after this. It releases resources and terminates the server's socket connection.

Reminders

Reminders are in a slightly different format from the Datasync protocol. The structure is as follows:

<reminders><reminder><start>T3T2T1T0</start><repeat>nn</repeat><for>nn</for></reminder> . . . </reminders> where . . . denotes more reminder records, each delineated by a <reminder></reminder> sequence. Each reminder block is part of the <control-entry> block. The <repeat> value is the number of seconds to repeat the reminder after the start. It is zero if there is no repetition. The <for> value is the number of times this repetition must be carried out. It too is zero if there is no repetition.

Chart Creation and Display

The chart creation and display mechanism is comprised of collaborating objects and components across all four application tiers (view, web, business object and data persistence tiers). As previously mentioned, Popchart is the charting server being used to render the data for display in the Flash format. This requires the Flash plug-in to be installed in the client browser, which the majority of the browsers (over 90%) already do.

The approach to chart creation and display is to isolate dependency on Popchart in the view tier only. This is to allow change over to another charting product if required later. Doing this requires encapsulating all code to create a Popchart chart in presentation components in the view tier. All the information (data) required to produce the chart is kept as generic objects or components and supplied to the view components via the standard application framework. This mechanism is elaborated upon below.

The View Tier

This tier is comprised of the JSP page containing the chart as well as an embedded JavaBean that converts the chart model objects into Popchart specific instructions (there may be the need to do specific JavaBeans for each chart type but the approach will remain the same for each). This JavaBean encapsulates the logic to create Popchart instructions from the chart model objects and isolates the dependency on Popchart.

The Popchart JSPExample demonstrates such a JSP/JavaBean combination. The key points of difference are:

The example code has a lot of hard-coded elements such as label information etc. All this information is being supplied in the chart model object(s) instead.

The example code has a lot of direct database access for retrieving data. All data required to create the chart will be supplied through the chart model object(s) or in objects directly associated with them. Some of these data objects would be the domain model objects themselves e.g. the Range object would contain the range of reading values to be charted.

The Web Tier

This tier contains the standard web handler for processing user input to the chart (such as when a user displays the chart, changes the date range, clicks on a point for annotation or drill-down etc.). The handler creates a chart event object (class ChartEvent) encapsulating the user request and forwards it to the Business Object tier for handling.

Note that there may be requests that can be handled in the web tier itself instead of having to go to the BO tier. For example, the user may choose to view a data range that is a subset of the range already displayed. In this case, there is no need to go to the BO tier to get data for display since the data has already been sent to the web tier in the chart model object(s). The web tier handlers need to be intelligent enough to check for these cases in order to improve application performance.

The Business Object Tier

This tier contains the components required to handle chart events generated from the web tier. The main facade component is a session BO named ChartManagerSBO. This BO interprets the chart event and creates/retrieves the chart model objects that are required to generate the requested chart. It invokes the ReadingsManager to get the actual readings model objects. This BO also provides the defaults for chart presentation.

The chart model objects also belong in this tier. These objects encapsulate the complete information required to render the chart. This includes information about the various chart display paramters as well references to the model objects that hold the actual data for display. The data used to populate the chart model is obtained from the chartconfig.xml file using a DAO implementing the ChartDAO interface.

The chart model object is mutable i.e. it can be changed when a user adds or changes annotations on data points. The annotation actually changes a particular reading referenced by the range, which is in turn referenced by the chart model object.

Implementation Notes

Popchart servlet redirector may be used.

The implementation DAO object actually is ChartXmlDAOImpl, meaning that it reads the XML configuration file.

The elements in the chart model object that are specific to the charting product are kept as properties so as to not make the structure of the model object dependent on product-specific attributes.

Patterns

Following are the design patterns utilized in the architecture. Further details can be found in publicly available J2EE Blueprints documents as well as in a book, entitled "Design Patterns", by Vlissides, Gamma, et al and are thus elaborated upon further here.

Model-View-Controller (MVC)

Data Access Object (DAO)

Bimodal Data Access

Front Component

Value Object

File Formats

Device Control File

This file is currently in plain text XML format. It may later be stored encrypted if necessary. It does not currently have a DTD and therefore requires a non-validating parser. For now, the URI for this file is file://c:\carematix\config\devicecontrol.xml.

```
<?xml version="1.0" encoding="ISO-8859-1"?>
<device-control-list>
  <control-entry>
    <device-id>
        <manufacturer-no>12345</manufacturer-no>
        <device-model>67890</device-model>
        <serial-no>555555555</serial-no>
        <user-no>1<user-no>
     </device-id>
    <last-update-timestamp>06-05-2001 11:21:33</last-update-
timestamp>
  </control-entry>
<!-- More <control-entry> records for all other devices that users of
  this PC have registered with Carematix.
-->
</device-control-list>
```

User Data File

This file is currently in plain text XML format. It may later be converted into a format in which each XML <reading-record> entry is encrypted and stored as a fixed length record, with new records being appended to the end. It does not currently have a DTD and therefore requires a non-validating parser. For now, the URI for this file is file://c:\carematix\data\readingsdata.xml.

Note: This file may contain duplicate <reading-record> entries. That is allowed.

```
<readings-data>
  <!-- Reading record for blood pressure and heart rate reading -->
  <reading-record>
    <device-id>
        <manufacturer-no>12345</manufacturer-no>
```

-continued

```
<device-model>67890</device-model>
<serial-no>555555555</serial-no>
<user-no>1<user-no>
</device-id>
<timestamp 06-05-2001 11:21:33 PM/>
<reading>
<!-- The reading-type tag may be eliminated later -->
<reading-type>BP-HR</reading-type>
<values>
<bp-systolic 120 />
<bp-diastolic 80 />
<pulse-rate 72 />
</values>
</reading>
</reading-record>
<!-- Reading record for temperature reading -->
<reading-record>
<device-id>
<manufacturer-no>29933</manufacturer-no>
<device-model>68909</device-model>
<serial-no>123456789</serial-no>
</device-id>
<timestamp 06-05-2001 11:21:42 PM/>
<reading>
<!-- The reading-type tag may be eliminated later -->
<reading-type>TEMP</reading-type>
<!-- The units for temperature are FARENHEIGHT
or CELCIUS -->
<units FARENHEIGHT />
<value 98.7 />
</reading>
</reading-record>
<!-- Reading record for weight reading -->
<reading-record>
<device-id>
<manufacturer-no>29890</manufacturer-no>
<device-model>68309</device-model>
<serial-no>123456789</serial-no>
</device-id>
<timestamp 06-05-2001 11:25:42 PM/>
<reading>
<!-- The reading-type tag may be eliminated later -->
<reading-type>WEIGHT</reading-type>
<!-- The units for weight are KILOGRAMS or POUNDS -->
<units KILOGRAMS />
<value 65 />
</reading>
</reading-record>
... more reading records from all devices (and all users)
</readings-data>
```

XML to iModem Tag Mappings

```
<tag-mapping type="request" xml-tag="readings-data" imodem-
tag="0000"/>
<tag-mapping type="request" xml-tag="reading-
record" imodem-tag="0001"/>
<tag-mapping type="request" xml-tag="reading" imodem
-tag="0002"/>
<tag-mapping type="request" xml-tag="reading-type" imodem-
tag="0003" byte-length="1">
<tag-token xml-token="BP-HR" imodem-token="04"/>
<tag-token xml-token="TEMP" imodem-token="05"/>
<tag-token xml-token="WEIGHT" imodem-token="06"/>
<tag-token xml-token="BLOODSUGAR" imodem-token="07"/>
</tag-mapping>
<tag-mapping type="request" xml-tag="values"
imodem-tag="0004"/>
<tag-mapping type="request" xml-tag="bp-systolic" imodem-
tag="0005" byte-length="1"/>
<tag-mapping type="request" xml-tag="bp-diastolic" imodem-
tag="0006" byte-length="1"/>
<tag-mapping type="request" xml-tag="pulse-rate" imodem-
tag="0007" byte-length="1"/>
<tag-mapping type="request" xml-tag="units" imodem-
tag="0008" byte-length="1">
<tag-token xml-token="mm Hg" imodem-token="00"/>
<tag-token xml-token="Kelvin" imodem-token="01"/>
<tag-token xml-token="POUNDS" imodem-token="02"/>
<tag-token xml-token="mg/dL" imodem-token="03"/>
```

-continued

```
</tag-mapping>
<tag-mapping type="response" xml-tag="current-
time" imodem-tag="0009" byte-length="4"/>
<tag-mapping type="common" xml-tag="device-id" imodem-
tag="000A"/>
<tag-mapping type="common" xml-tag="manufacturer-
no" imodem-tag="000B" byte-length="3"/>
<tag-mapping type="common" xml-tag="device-
model" imodem-tag="000C" byte-length="3"/>
<tag-mapping type="common" xml-tag="serial-no" imodem-
tag="000D" byte-length="4"/>
<tag-mapping type="common" xml-tag="user-no" imodem-
tag="000E" byte-length="1"/>
<tag-mapping type="common" xml-tag="device-control-
list" imodem-tag="000F"/>
<tag-mapping type="response" xml-tag="control-
entry" imodem-tag="0091"/>
<tag-mapping type="response" xml-tag="reminders" imodem-
tag="0092"/>
<tag-mapping type="response" xml-tag="reminder" imodem-
tag="0093"/>
<tag-mapping type="response" xml-tag="start" imodem-
tag="0094" byte-length="4"/>
<tag-mapping type="response" xml-tag="repeat" imodem-
tag="0095"byte-length="4"/>
<tag-mapping type="response" xml-tag="for" imodem-
tag="0096" byte-length="1"/>
<tag-mapping type="request" xml-tag="timestamp" imodem-
tag="0097"byte-length="4"/>
<tag-mapping type="response" xml-tag="first-association-timestamp"
imodem-tag="0098" byte-length="4"/>
<tag-mapping type="response" xml-tag="last-update-timestamp"
imodem-tag="0099" byte-length="4"/>
<tag-mapping type="response" xml-tag="status" imodem-
tag="009A"byte-length="2"/>
<tag-mapping type="common" xml-tag="device-
info" imodem-tag="009B">
<tag-mapping type="response" xml-tag="num-
devices" imodem-tag="009C" byte-length="1"/>
<tag-mapping type="request" xml-tag="device-
num" imodem-tag="009D" byte-length="1"/>
<tag-mapping type="common" xml-tag="initiate-
session" imodem-tag="0030"/>
<tag-mapping type="request" xml-tag="hub-id" imodem-
tag="0031" byte-length="4"/>
<tag-mapping type="request" xml-tag="protocol-
version" imodem-tag="0032" byte-length="2"/>
<tag-mapping type="response" xml-tag="update-
flag" imodem-tag="0033" byte-length="1"/>
<tag-mapping type="response" xml-tag="key" imodem-
tag="0034" byte-length="2"/>
<tag-mapping type="common" xml-tag="terminate-
session" imodem-tag="0035"/>
<tag-mapping type="common" xml-tag="param-
updates" imodem-tag="0036"/>
```

Chart Configuration File

This file contains the necessary information for formatting and displaying data charts. This information is kept in XML format neutral of the specific charting product so as to allow changeover to another charting application if necessary later. It does not currently have a DTD and therefore requires a non-validating parser. This file is stored on the server, not the client and is called chartconfig.xml Please note the following: this format is an initial version and will likely be enhanced over time. The method for altering and enhancing chart display is to add tags and/or properties in the sections for each chart and use the values assigned to each to drive the behavior of the code. This is preferred over hard-coding the way a chart is displayed in the code itself.

In subsequent phases, this file may have an XSL transform applied to generate the product specific charting instructions e.g. if using Popchart, an XSLT would be provided to generate PCScript from this XML file.

```
<chart-config>
  <bp-chart>
    <type>TIMELINE</type>
    <title>Blood Pressure</title>
    <height>xxx</height>
    <width>yyy</width>
    <property name="appearance-file" value=
    "URL of appearance file" />
    <property name="date-format" value="%m/%d/%y %H:%M" />
  </bp-chart>
  <hr-chart>
    <type>TIMESCATTER</type>
    <title>Heart Rate</title>
    <height>xxx</height>
    <width>yyy</width>
    <property name="appearance-file" value=
    "URL of appearance file" />
    <property name="date-format" value="%m/%d/%y %H:%M" />
  </hr-chart>
  <temperature-chart>
    <type>TIMELINE</type>
    <title>Temperature</title>
    <height>xxx</height>
    <width>yyy</width>
    <property name="appearance-file" value=
    "URL of appearance file" />
    <property name="date-format" value="%m/%d/%y %H:%M" />
  </temperature-chart>
  <weight-chart>
    <type>TIMELINE</type>
    <title>Blood Pressure</title>
    <height>xxx</height>
    <width>yyy</width>
    <property name="appearance-file" value=
    "URL of appearance file" />
    <property name="date-format" value="%m/%d/%y %H:%M" />
  </weight-chart>
</chart-config>
```

Obviously, many modifications and variations of the present invention are possible in light of the above teachings. Thus, it is to be understood that, within the scope of the appended claims, the invention may be practiced otherwise than as specifically described above.

What is claimed and desired to be covered by a Letters Patent is as follows:

What is claimed:

1. A patient monitoring system comprising:

one or more patient monitoring devices for one or more patients, each patient monitoring device including a physiological transducer monitoring physiological characteristic data of said one or more patients and storing said physiological characteristic data in a device memory, and a first wireless communication system automatically transmitting and synchronizing said physiological characteristic data to a common hub over a first communication link, wherein said physiological data is associated with a time stamp representing a time reading from an internal microprocessor taken when said physiological characteristic data is recorded, wherein said synchronizing includes comparing said time stamp with a time stamp received from a common hub and transmitting said physiological characteristic data and said associated time stamp to said hub only when said time stamp indicates a time after said time stamp received from said hub, wherein said physiological characteristic data and associated time stamp are deleted from said device memory when said associated time stamp represents a time earlier than said time stamp received from said hub;

wherein said internal microprocessor receives an indication of the current time from said hub and updates its time to the current time received from said hub;

a common hub remote from said patient monitoring devices and including a second communication system automatically receiving and synchronizing said physiological characteristic data from said patient monitoring devices and exchanging messages with said patient monitoring devices over said first communication link from said one or more patient monitoring devices and automatically transmitting and synchronizing said physiological characteristic data, received from said patient monitoring devices, to a remote server over a second communication link, wherein synchronizing said hub with said patient monitoring device includes transmitting a time stamp stored at said hub to said patient monitoring device, wherein said time stamp stored at said hub is previously received from said remote server;

wherein synchronizing said hub with said remote server includes receiving a time stamp from said remote server and replacing said time stamp stored at said hub with said time stamp from said remote server, and wherein said hub receives a current time indication from said remote server and updates an internal hub microprocessor to said current time indication, wherein a time indication from said internal hub microprocessor is later sent to said patient monitoring device to update the current time at said patient monitoring device; and a remote server including a third communication system receiving said physiological characteristic data from said hub over said second communication link, which automatically synchronizes said physiological characteristic data from said common hub and exchanges messages with said common hub over said second communication link, wherein said server receives a time stamp associated with said physiological characteristic data from said hub, wherein said server compares the time reading of said time stamp to a time reading of a previously received time stamp associated with physiological characteristic data, wherein said server discards said physiological characteristic data and said time stamp when said time reading of said time stamp is earlier than said time reading of said previously received time stamp, wherein said server transmits the later of said time stamp and said previously received time stamp to said hub to synchronize said physiological characteristic data from said common hub, and wherein said remote server transmits an indication of the current time to said hub.

2. The patient monitoring system as recited in claim 1, wherein said second communication link includes a public communication network.

3. The patient monitoring system as recited in claim 1, wherein said second communication link includes a private communication network.

4. The patient monitoring system as recited in claim 1, wherein said remote server is also configured as a web portal.

5. The patient monitoring system as recited in claim 1, wherein said first communication system and said second communication system are bi-directional.

6. The patient monitoring system as recited in claim 5, wherein said remote server is configured to transmit data to said patient monitoring device under predetermined conditions.

7. The patient monitoring system as recited in claim 6, wherein said data includes patient reminders to take reading at predetermined times.

8. The patient monitoring system as recited in claim 1, wherein said remote server is configured to provide a notification under predetermined conditions by way of a separate notification system.

9. The patient monitoring system as recited in claim 8, wherein said separate notification system is email.

10. The patient monitoring system as recited in claim 8, wherein said separate notification system is a pager.

11. The patient monitoring system as recited in claim 8, wherein said notification is provided to a patient.

12. The patient monitoring system as recited in claim 8, wherein said notification is provided to a third party.

13. The patient monitoring system as recited in claim 4, wherein said web portal is configured to provide third-party access to said physiological characteristic data.

14. The patient monitoring system as recited in claim 6, wherein said data includes alarm threshold values for said physiological characteristic data and said patient monitoring device includes an alarm which indicates when patient physiological characteristic data exceeds said alarm threshold value.

15. The patient monitoring system as recited in claim 1, wherein said physiological characteristic data is continuously monitored.

16. The patient monitoring system as recited in claim 1, wherein said physiological characteristic data is periodically monitored.

17. The patient monitoring system as recited in claim 1, wherein said physiological characteristic data is continuously transmitted over said first and second communication links.

18. The patient monitoring system as recited in claim 1, wherein said physiological characteristic data is periodically transmitted over said first and second communication links.

19. The patient monitoring system as recited in claim 8, wherein said separate notification system is a cellular phone.

20. The patient monitoring system as recited in claim 5, wherein an alarm is transmitted to the patient monitoring device when one or more instances of predetermined physiological data are not received over a predetermined time period.

21. The patient monitoring system as recited in claim 5, wherein confirmation of receipt of physiological data is provided to said patient monitoring device by said hub.

22. The patient monitoring system as recited in claim 5, wherein confirmation of receipt of physiological data is provided by said remote server.

23. The patient monitoring system as recited in claim 1, wherein said hub is configured to receive and segregate physiological data from two or more patients.

24. The patient monitoring system as recited in claim 1, wherein at least one of said one or more patient monitoring devices includes a real time clock.

25. The patient monitoring system as recited in claim 24, wherein said hub is configured to synchronize said real time clock in said at least one of said one or more patient monitoring devices.

26. The patient monitoring system as recited in claim 5, wherein confirmation of receipt of physiological data is provided to said hub by said remotes server.

27. A patient monitoring system comprising:

one or more patient monitoring devices for one or more patients, each patient monitoring device including a physiological transducer monitoring physiological characteristic data of said one or more patients and storing said physiological characteristic data in a device memory, and a first wireless communication system automatically transmitting and synchronizing said physiological characteristic data to a common hub over a first communication link, wherein said physiological data is associated with a time stamp representing a time reading from an internal microprocessor taken when said physiological characteristic data is recorded, wherein said synchronizing includes comparing said time stamp with a time stamp received from a common hub and transmitting said physiological characteristic data and said associated time stamp to said hub only when said time stamp indicates a time after said time stamp received from said hub, wherein said physiological characteristic data and associated time stamp are deleted from said device memory when said associated time stamp represents a time earlier than said time stamp received from said hub;

wherein said internal microprocessor receives an indication of the current time from said hub and updates its time to the current time received from said hub;

a common hub remote from said patient monitoring devices and including a second communication system automatically receiving and synchronizing said physiological characteristic data from said patient monitoring devices and exchanging messages with said patient monitoring devices over said first communication link from said one or more patient monitoring devices and automatically transmitting and synchronizing said physiological characteristic data, received from said patient monitoring devices, to a remote server over a second communication link, wherein synchronizing said hub with said patient monitoring device includes transmitting a time stamp stored at said hub to said patient monitoring device, wherein said time stamp stored at said hub is previously received from said remote server;

wherein synchronizing said hub with said remote server includes receiving a time stamp from said remote server and replacing said time stamp stored at said hub with said time stamp from said remote server, and wherein said hub receives a current time indication from said remote server and updates an internal hub microprocessor to said current time indication, wherein a time indication from said internal hub microprocessor is later sent to said patient monitoring device to update the current time at said patient monitoring device; and a remote server including a third communication system receiving said physiological characteristic data from said hub over said second communication link, which automatically synchronizes said physiological characteristic data from said common hub and exchanges messages with said common hub over said second communication link, and wherein said remote server transmits an indication of the current time to said hub.

* * * * *